United States Patent [19]

Mazur

[11] 4,273,704

[45] Jun. 16, 1981

[54] N-ADAMANTANE-SUBSTITUTED TETRAPEPTIDE AMIDES

[75] Inventor: Robert H. Mazur, Deerfield, Ill.

[73] Assignee: G. D. Searle & Co., Chicago, Ill.

[21] Appl. No.: 99,765

[22] Filed: Dec. 3, 1979

[51] Int. Cl.³ .......................................... C07C 103/52
[52] U.S. Cl. .......................................... 260/112.5 R
[58] Field of Search ................................ 260/112.5 R

[56] References Cited

FOREIGN PATENT DOCUMENTS 2732451 7/1977 Fed. Rep. of Germany .... 260/112.5 R

*Primary Examiner*—Delbert R. Phillips

*Attorney, Agent, or Firm*—Mary Jo Kanady; W. Dennis Drehkoff

[57] ABSTRACT

N-Adamantane-substituted tetrapeptide amides and the pharmacologically acceptable salts thereof are disclosed herein. These compounds are analogs of enkephalin wherein the methionine or leucine of position 5 has been substituted by an adamantyl amide and the glycine of position 2 has been substituted by various amino acid residues. Optionally the tyrosine of position 1 and the phenylalanine of position 4 may be substituted by various amino acid residues. These compounds exhibit agonist activity at opiate receptor sites and are useful as analgesics.

17 Claims, No Drawings

N-ADAMANTANE-SUBSTITUTED TETRAPEPTIDE AMIDES

BACKGROUND OF THE INVENTION

1. Field of the Invention

The present invention relates to N-adamantane-substituted tetrapeptide amides and the pharmacologically acceptable salts thereof. These compounds are analogs of enkephalin wherein the methionine or leucine of position 5 has been substituted by an adamantyl amide and the glucine of position 2 has been substituted by various amino acid residues. Optionally, the tyrosine of position 1 and the phenylalanine of position 4 may also be substituted by various amino acid residues. Enkephalin, a naturally occurring pentapeptide, has been isolated and found to be a mixture of two pentapeptides which differ only in the fifth amino acid residue. Leucine $^5$-enkephalin is represented by the following formula

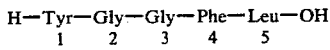

and methionine $^5$-enkephalin is represented by the formula

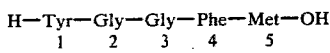

wherein the Tyr, Phe, Met, and Leu residues are all of the L-stereochemical configuration.

2. Description of the Prior Art

R. Tomatis, et. al., IL FARMACO-ED.Sc., 34(6): 496–506 (1979) describes the synthesis of Leu-enkephalin-1-adamantylamide and Leu-[D-Ala$^2$]enkephalin-1-adamantylamide. These compounds are structurally distinct from the compounds of the present invention in that they disclose 1-adamantyl amide attached to the entire enkephalin molecule whereas the present invention teaches the replacement of the amino acid in position 5 of enkephalin with an adamantyl amide.

K.Q.Do, et. al., HELVETICA CHIMICA ACTA 62(4):956–964 (1979) describes the synthesis of (S)-(+)-2-amino-3-(1-adamantyl)-propionic acid, a compound in which the phenyl radical of phenylalanine is substituted by adamantane. The present invention describes novel N-adamantane-substituted tetrapeptide amides. These compounds are analogs of enkephalin in which the 5-position is substituted by an adamantyl amide. The adamantyl amide residues of the compounds of the present invention are structurally different from (S)-(+)-2-amino-3-(1-adamantyl)-propionic acid in that the amino radical and the carboxyl radical when present are attached directly to the adamantane radical.

SUMMARY OF THE INVENTION

The present invention is concerned with novel N-adamantane substituted tetrapeptide amides, derivatives thereof, and their pharmacologically acceptable salts. More particularly this invention is concerned with compounds of the formula

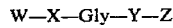 (I)

wherein W represents tyrosine or a radical of the formula

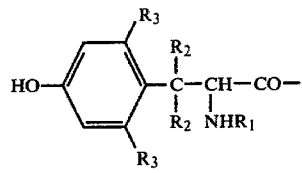

wherein $R_1$, $R_2$, and $R_3$ may each independently by hydrogen or an alkyl group having 1 to 4 carbon atoms;

X represents methionine, methionine sulfoxide, dehydroaminobutyric acid, 1-aminocyclopropane carboxylic acid, alanine, O-methylhomoserine, proline or norleucine;

Y represents phenylalanine, dehydrophenylalanine, cyclohexylalanine, or a radical of the formula

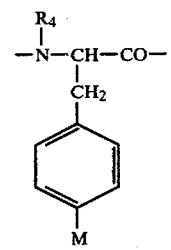

wherein $R_4$ represents hydrogen or an alkyl group having 1 to 4 carbon atoms and M represents hydrogen, nitro, or halogen; and Z represents a radical of the formula

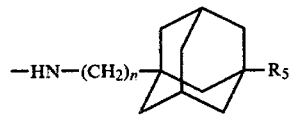

wherein $R_5$ represents hydrogen, carboxyl, methoxycarbonyl, carboxamide or hydroxymethyl and n is 0, or 2; a radical of the formula

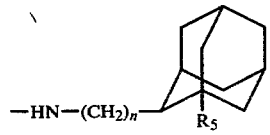

wherein $R_5$ and n are defined as hereinbefore; a radical of the formula

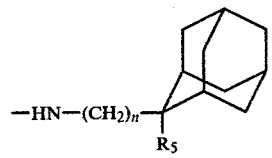

wherein $R_5$ and n are defined as hereinbefore; a radical of the formula

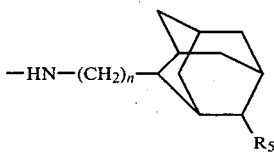

wherein $R_5$ and n are defined as hereinbefore; a radical of the formula

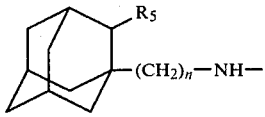

wherein $R_5$ and n are defined as hereinbefore, or a radical of the formula

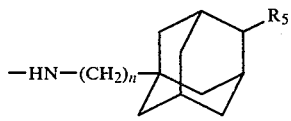

wherein $R_5$ and n are defined as hereinbefore; the stereochemical configuration of each of the optically active amino acid residues may independently be D, L, or DL; and the pharmacologically acceptable salts thereof.

Abbreviations connote the amino acids defined in accordance with the nomenclature rules published by the IUPAC-IUB Commission on Biochemical Nomenclature in Biochem. J. 126: 773–780(1972). The amino acids have the L-stereochemical configuration unless otherwise indicated. It would be apparent to one skilled in the art that many variations in the substituent group ($R_5$) on the adamantane radical would be possible without affecting the pharmacological activity of the present compounds, and that it would be possible to have more than one substituent group on the adamantane radical, which groups could be alike or different, without affecting the pharmacological activity. A number of possible substituent groups are disclosed in the 1979–1980 Aldrich Catalog Handbook of Fine Chemicals at pages 21–22. Possible substituent groups include but are not limited to halogen, nitro, hydroxy, tetrazole, amino, oxo, $-CH_2OB(OH_2)$ $-NHCOCH_3$, $-(CH_2)_{0-4}NH_2$, $-O(CH_2)_{1-4}CH_3$, $-SO_3CH_3$, $-(CH_2)_{0-4}CHO$, $-(CH_2)_{0-4}CH_3$, $-(CH_2)_{0-4}CN$, $-(CH_2)_{0-4}COOH$, $-COCl$, $-COCH_3$, $-NHCONH_2$, $-(CH_2)_{0-4}OH$, and $-N=C=S$.

Equivalent to the enformulated compounds for the purposes of this invention are solvates thereof in which biologically insignificant amounts of solvent are present.

Also equivalent to the compounds of formula (I) for the purposes of this invention are the pharmaceutically acceptable acid addition salts thereof. Such acid addition salts can be derived from a variety of inorganic and organic acids such as sulfuric, phosphoric, hydrochloric, hydrobromic, hydriodic, nitric, sulfamic, citric, lactic, pyruvic, oxalic, maleic, succinic, tartaric, cinnamic, acetic, trifluoroacetic, benzoic, salicylic, gyconic, ascorbic and related acids.

The compounds of the present invention are useful in consequence of their valuable pharmacological properties. They are, for example, agonists at opiate receptor sites and are useful as analgesics.

The assay utilized for detection of the agonist activity at opiate receptor sites is a modification of the technique described by Pert, Snowman and Snyder, in *Brain Research*, 70, 184(1974).

Details of that assay are as follows: An albino guinea pig of either sex, weighing 300–400 grams, is killed by cervical dislocation, the brain removed and the cerebellum discarded. The remaining tissue is chilled, weighed and homogenized in 30 ml of 0.32 M sucrose with a teflon-glass homogenizer. The homogenate is centrifuged for 10 minutes at 4° C. at 1000 g in a Sorvall RC-2B centrifuge. The resultant supernatant is decanted and centrifuged for 30 minutes at 4° C. at 20,000 g. The resultant pellet is washed by resuspension in 0.05 M tris-HCl buffer (pH 7.4) and then centrifuged for 30 minutes at 4° C. at 20,000 g. The final pellet is suspended in 30 ml of buffer per brain for assay. For assays in the presence of sodium ion, the buffer is Krebs-tris, pH 7.4, while in the absence of sodium the buffer is 0.05 M tris-HCl, pH 7.4. Levorphanol ($10^{-6}$ M) and dextrorphan ($10^{-6}$ M) are used to determine specific binding. Receptor binding activity is determined as described by Pert and Snyder with some modifications. $^3$H-(−)-naloxone (19.985 Ci/mmole, lot # 887-201, New England Nuclear Corp, Boston, Mass.) is used as the radioligand. The washed membrane fraction is diluted 1:10 in appropriate buffer and 2 ml per tube is used in the assay. Binding studies are initiated by preincubation of the homogenate containing varying concentrations (in triplicate) of the test compound or standard on ice (4° C.) for 10 minutes. The reaction is initiated by addition of the $^3$H-naloxone (final concentration, 2.5 nM) to the tube and incubation on ice for an additional 30 minutes. Samples are filtered rapidly under reduced pressure onto Whatman GF/C glass fiber filter discs. The filers are washed twice with 8 ml of ice cold buffer and then solubilized in 1 ml of NCS$^{TM}$ tissue solubilizer (Amersham/Searle Corp., Arlington Heights, Ill.) for 1 hr. at 55° C. After cooling, samples are acidified and counted in a liquid scintillation counter (Mark II Nuclear Chicago). An ID$_{50}$ concentration of the drug inhibiting $^3$H-naloxone binding is determined from log-probit curves of the percent inhibition of $^3$H-naloxone binding versus concentration of the test compound.

The in vitro assay described is widely known to correlate with related agonist-antagonist properties in vivo (*Nature*, vol. 247, Jan. 11, 1974). When a known agonist, morphine, was tested by this assay, in the absence of sodium ion, it had an ID$_{50}$ concentration of $7.4 \times 10^{-7}$.

It is also known that the receptor affinities in the ileum are similar in their binding characteristics with those of the brain [Terenius, *Acta. Pharmacol. et Toxicol.*, 37, 211–221 (1975)]. Available evidence indicates that drugs which act on the ileum opiate receptors cause constipation, and are therefore useful as antidiarrheal agents.

The analgesic activity of compounds of the present invention may be demonstrated using the mouse, phenyl-p-benzoquinone-induced writhing test. This test is a modification of the procedure described by L. C. Hendershot and J. Forsaith, in J. PHARMACOL. EXP. THER., 125:237(1959).

Details of the test are as follows: Groups of 10 male CD-1 mice (Charles River) weighing 18–25 g. are pretreated subcutaneously (s.c.) or intragastrically (i.g.)

with the vehicle control or the compound of interest in a volume of 10 ml/kg. Phenyl-p-benzoquinone (PBQ), 2.5 mg/kg is administered intraperitoneally (i.p.) 30 or 60 minutes later as a 0.025% solution in 5% ethanol. Starting 5 minutes after the PBQ challenge, each mouse is observed for a 10 minute period during which the number of writhes are counted. A "writhe" consists of a combination or sequence of arching the back, pelvic rotation, and hind limb extension. Significant analgesia is assumed when an animal writhing frequency is $\leq 50\%$ of the daily control group mean. Estimates of the $ED_{50}$ defined as the dose which decreased writhing by $\geq 50\%$ of the control group mean in 50% of the mice are determined using the method of J. T. Litchfield and F. Wilcoxon, J. PHARMCOL. EXP. THER., 96:99(1949). When morphine was tested s.c. in the writhing mouse test it exhibited an $ED_{50}$ (95% confidence limits), 60 minutes, of 0.1 mpk. When a representative compound of the present invention, methyl 2,6-dimethyl-DL-tyrosyl-D-methionyl-glycyl-L-phenylalanyl-3-amino-1-adamantane-carboxylate was tested s.c., it exhibited an $ED_{50}$ (95% confidence limits), 60 minutes, of 0.31(0.13–0.74)mpk.

The compounds of the present invention may be combined with various typical pharmaceutical carriers to provide compositions suitable for use as analgesics. The dosage of these compounds is dependent upon various factors, such as the particular compound employed and the particular response obtained. Typical dosage for use as an analgesic may vary from 0.3–10 mg/kg per day administered parenterally.

The manufacture of the instant novel compounds is conveniently achieved by processes adapted to the synthesis of peptides, i.e., both solution syntheses and solid phase peptide synthesis. In the case of solution synthesis the order in which the amino acids are coupled is not critical and the tetrapeptide adamantyl amide may be produced by coupling any two suitable units containing the desired amino acids or adamantyl amide.

The compounds of the present invention may be prepared by the mixed anhydride coupling procedure described in G. W. Anderson, et. al., J. AM. CHEM. SOC., 88:1338(1966). Thus an N-protected amino acid or peptide is dissolved in an inert solvent. Suitable solvents include but are not limited to tetrahydrofuran, dichloroethane, and ethyl acetate. One equivalent of a tertiary amine such as N-methylmorpholine or N-ethylmorpholine is added and the solution is cooled to about $-20°$ C. One equivalent of isobutylchloroformate or ethylchloroformate is added dropwise with stirring while maintaining the temperature below $-10°$ C. After about 5 minutes the compound to be coupled, i.e., an amino acid, peptide, or adamantyl amide is added as the free base (or as a salt along with one equivalent of N-methylmorpholine). The reaction mixture is stirred at room temperature until the reaction is complete. The reaction is normally essentially complete after a period of from 2 to 24 hours but may be carried out for longer periods to insure completeness. The N-blocked product is then deprotected in a conventional manner to give the desired product. The reaction is illustrated by the following scheme wherein W, X, Y and Z are defined as hereinbefore and □ represents an N-protecting group:

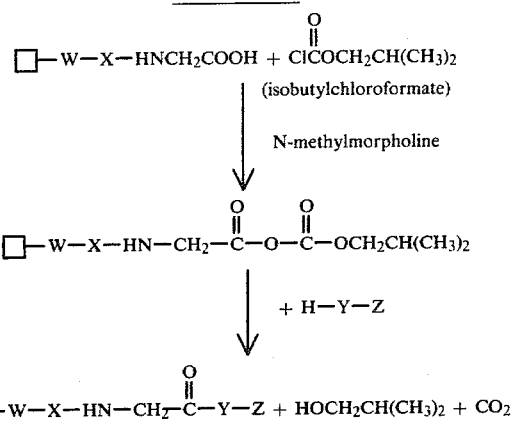

SCHEME 1

Alternatively, the compounds of the present invention may be prepared by solid phase peptide synthesis procedures well known in the art such as described by Merrifield, J. AM. CHEM. SOC., 85, 2149(1963). This procedure consists of first attaching to a polymer support, e.g., a chloromethylated copolymer, styrene-1% divinylbenzene, the N-protected C-terminal amino acid, followed by removal of the N-protecting group, and coupling, in the presence of a suitable dehydrating agent, e.g., dicyclohexylcarbodiimide, successively with each of the appropriate N-protected amino acids.

The amino functions of the intermediates of this invention may be protected by commonly used amino protecting groups such as aryl-lower alkyl groups. Such groups may be diphenylmethyl or triphenylmethyl groups, which are optionally substituted by halogen, nitrogen, lower alkyl or lower alkoxy, for example; benzhydryl, trityl and di-paramethoxybenzhydryl; acyl groups, such as formyl, trifluoroacetyl, phthaloyl, p-toluenesulphonyl; groups derived from carbonic acid or thiocarbonic acid, such as carbobenzoxy groups which are optionally substituted in the aromatic radical by halogen, nitro groups or lower alkyl, lower alkoxy or lower carbalkoxy groups, for example, carbobenzoxy (Cbz), p-bromocarbobenzoxy or p-chlorocarbobenzoxy, p-nitrocarbobenzoxy and p-methoxycarbobenzoxy; coloured benzyloxycarbonyl groups such as p-phenylazobenzyloxycarbonyl and p-(p-methoxyphenylazo)-benzyloxycarbonyl, tolyloxycarbonyl, 2-phenyl-2- propoxycarbonyl, 2-tolyl-2-propoxycarbonyl; and 2-(parabiphenylyl)-2-propoxycarbonyl; and aliphatic oxycarbonyl groups, such as t-butoxycarbonyl (Boc), allyloxycarbonyl, cyclopentyloxycarbonyl, t-amyloxycarbonyl. A particularly preferred N-protecting group for use in this invention is the t-butoxycarbonyl (Boc) group.

The amino groups can also be protected by forming enamines, obtained by reaction of the amino groups with 1,3-diketones, for example, benzoylacetone, or acetylacetone.

Protecting groups are conveniently removed by reactions such as reduction with sodium in liquid ammonia, hydrogenolysis (for instance, in the presence of a palladium black catalyst), treatment with a hydrohalo acid (such as hydrochloric, hydrobromic, hydrofluoric or hydriodic acids) in acetic acid, or treatment with trifluoroacetic acid.

The following examples described in detail the preparation of compounds illustrative of the present invention. It will be apparent to those skilled in the art that many modifications, both of materials and methods, may be practiced without departing from the purpose and intent of this disclosure. Throughout the examples hereinafter set forth, temperatures are given in degrees Centigrade (°C.) and relative amounts in grams or milliliters unless otherwise noted.

EXAMPLE 1

3-amino-1-adamantanecarboxylic acid is prepared by the method described in Loevens Kemiske Fabrik Produktionsaktieselskab, Netherlands Application 6,512,491; Mar. 29, 1966 CHEM. ABS. 65: 16975(1966) and 3.90 g is added to a soluton of 3.6 ml thionyl chloride in 125 ml of methanol. The reaction mixture is heated overnight under reflux and the methanol is distilled off under vacuum. The residue is shaken with ether to yield methyl 3-amino-1-adamantanecarboxylate hydrochloride which has the following structural formula

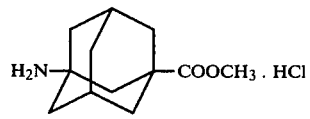

EXAMPLE 2

To 30 ml of a 1 N sodium hydroxide solution is added 4.95 g of L-phenylalanine. The solution is cooled and stirred in an ice bath and 5.4 ml of a 6.1 M solution of carbobenzoxychloride is added dropwise along with additional 1 N sodium hydroxide solution so that the pH remains at 11.0–11.5. The reaction mixture is washed with ether. The aqueous layer is acidified to pH 1.0 with 12 N hydrochloric acid, then the solution is extracted with ethyl acetate. The ethyl acetate extract is separated and is washed three times with water then dried over magnesium sulfate. The solvent is removed under vacuum. The residue crystallizes on rubbing with water to give N-carbobenzoxy-L-phenylalanine. 3.99 Grams of methyl 3-amino-1-adamantanecarboxylate hydrochloride and 4.78 g of carbobenzoxy-L-phenylalanine are dissolved in 40 ml methylene chloride. To this solution is added 1.8 ml of N-methylmorpholine followed immediately by 2.19 g of dicyclohexylcarbodiimide. The reaction mixture is allowed to stand for 24 hours at room temperature, then the treatment with carbobenzoxy-L-phenylalanine and dicyclohexylcarbodiimide is repeated. The reaction mixture is again allowed to stand for 24 hours at room temperature. The dicyclohexylurea is removed by filtration and washed with methylene chloride. The combined filtrates are washed twice with 0.5 M potassium bisulfate, water and 1 M solution of potassium bicarbonate and dried over magnesium sulfate. The dicloromethane is removed under vacuum and the residue is purified by low pressure chromatography on silica gel using mixtures of hexane and chloroform as eluting solvent to give methyl carbobenzoxy-L-phenylalanyl-3-amino-1-adamantanecarboxylate which has the following structural formula

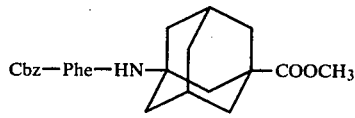

wherein Cbz represents carbobenzoxy.

EXAMPLE 3

To 3.58 grams of methyl carbobenzoxy-L-phenylalanyl-3-amino-1-adamantanecarboxylate dissolved in 10 ml of acetic acid is added 15 ml of a 5 M solution of hydrogen bromide in acetic acid, and the reaction mixture is allowed to stand for one hour at room temperature. The solvent is removed by distillation under vacuum and the residue is shaken with two 100 ml portions of hexane, then 100 ml of ether, to give methyl L-phenylalanyl-3-amino-1-adamantanecarboxylate hydrobromide which has the following structural formula

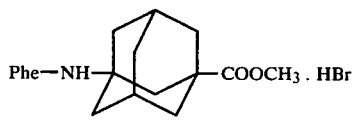

EXAMPLE 4

The crude methyl L-phenylalanyl-3-amino-1-adamantanecarboxylate hydrobromide from Example 3 is dissolved in 15 ml of dimethylformamide. To this solution is added 1.12 ml of N-methylmorpholine followed by 2.18 g of t-butoxycarbonylglycine N-hydroxysuccinimide ester. The reaction mixture is allowed to stand for 24 hours at room temperature and is then diluted with 300 ml of ethyl acetate. The ethyl acetate layer is washed with 0.5 M potassium bisulfate followed by washes with water, 0.5 M potassium bicarbonate, and water dried over magnesium sulfate. The solution is filtered to remove the magnesium sulfate, and the solvent is removed. Purification of the residue by low pressure chromatography on silica gel gives methyl Boc-glycyl-L-phenylalanyl-3-amino-1-adamantanecarboxylate which is represented by the following formula

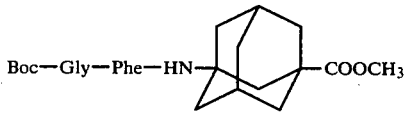

EXAMPLE 5

To 3.65 g of methyl Boc-glycyl-L-phenylalanyl-3-amino-1-adamantanecarboxylate dissolved in 20 ml of dioxane is added 10 ml of a 6 M solution of hydrogen chloride in dioxane. The reaction mixture is allowed to stand for 30 minutes at room temperature, the solvent is removed and the residue shaken with ether. Removal of the ether gives a white powder which is methyl glycyl-L-phenylalanyl-3-amino-1-adamantanecarboxylate hydrochloride which is represented by the following formula

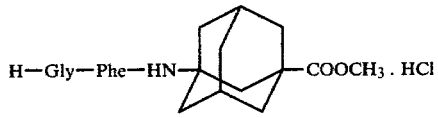

EXAMPLE 6

A mixed anhydride is prepared by reacting 2.0 g of Boc-D-methionine with 0.90 ml of N-methylmorpholine and 1.06 ml isobutylchloroformate in 15 ml of tetrahydrofuran at −20° C. A solution of 2.84 g of methyl glycyl-L-phenylalanyl-3-amino-1-adamantanecarboxylate hydrochloride in 15 ml tetrahydrofuran is neutralized with 0.78 ml N-methyl morpholine and added to the mixed anhydride reaction above. The reaction mixture is stirred for 2 hours at room temperature and allowed to stand overnight. The reaction mixture is diluted with 200 ml of ethyl acetate. The ethyl acetate layer is collected and washed with water, followed by washes with 0.2 M potassium bisulfate, water, and 1 M potassium bicarbonate and dried over magnesium sulfate. The solution is filtered and the solvent removed under reduced pressure. Purification of the residue by low pressure chromatography on silica gel affords methyl Boc-D-methionyl-glycyl-L-phenylalanyl-3-amino-1-adamantanecarboxylate which is represented by the following formula

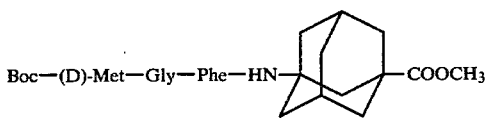

EXAMPLE 7

A solution of 3.383 g of methyl Boc-D-methionyl-glycyl-L-phenylalanyl-3-amino-1-adamantanecarboxylate in 15 ml of dioxane is allowed to react with 10 ml of a 6 M solution of hydrogen chloride in dioxane for 30 minutes at room temperature. The dioxane is removed and the residue is dried in a vacuum desiccator to give the deblocked peptide which is methyl D-methionyl-glycyl-L-phenylalanyl-3-amino-1-adamantanecarboxylate hydrochloride. This compound is represented by the formula

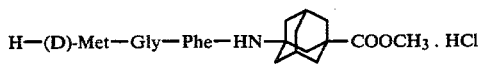

EXAMPLE 8

To a solution of 3.513 g of methyl D-methionylglycyl-L-phenylalanyl-3-amino-1-adamantanecarboxylate hydrochloride in 30 ml of tetrahydrofuran is added 3.17 g of Boc-L-tyrosine pentachlorophenyl ester followed by 1.12 ml of N-methylmorpholine. The reaction mixture is allowed to stand for 4 hours at room temperature then diluted with 200 ml ethyl acetate. The ethyl acetate layer is separated and washed three times with a 0.5 M solution of potassium bisulfate then dried over magnesium sulfate. The solvent is removed under reduced pressure and the residue is purified by low pressure chromatography on silica gel to give methyl Boc-L-tyrosyl-D-methionyl-glycyl-L-phenylalanyl-3-amino-1-adamantanecarboxylate which is represented by the following formula

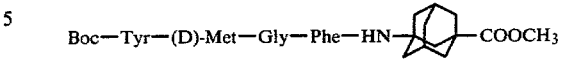

EXAMPLE 9

To a mixture of 5.0 ml acetic acid, 5.0 ml dioxane and 10.0 ml of a 6 M solution of hydrogen chloride in dioxane is added 1.0 g of methyl Boc-L-tyrosyl-D-methionyl-glycyl-L-phenylalanyl-3-amino-1-adamantanecarboxylate. The reaction mixture is allowed to stand for 30 minutes at room temperature then the solvent is removed by vacuum distillation. The residue is dissolved in a mixture of 2.0 ml methanol and 20 ml water and the solution is lyophilized to give methyl L-tyrosyl-D-methionyl-glycyl-L-phenylalanyl-3-amino-1-adamantanecarboxylate hydrochloride which is represented by the following formula

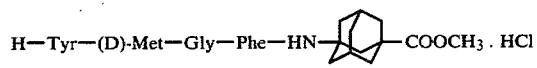

EXAMPLE 10

0.285 Grams of methyl L-tyrosyl-D-methionylglycyl-L-phenylalanyl-3-amino-1-adamantanecarboxylate hydrochloride is dissolved in a mixture of 2.0 ml of methanol and 2.0 ml of water, and 0.1 ml of 30% hydrogen peroxide is added. The reaction mixture is allowed to stand for 1 hour at room temperature, then 20 ml of water is added and the mixture is lyophilized to give methyl L-tyrosyl-D-methionyl-glycyl-L-phenylalanyl-3-amino-1-adamantanecarboxylate sulfoxide hydrochloride which is represented by the following formula

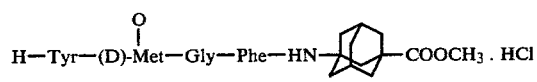

EXAMPLE 11

The hydrochloride addition salt of Example 9 may be converted into other suitable salts or the free base by standard procedures such as ion exchange methods.

For example, a weakly basic ion exchange resin such as 1R-45 is converted to the acetate form by the following procedure:
  a. Wash with 2 N sodium hydroxide
  b. Wash until neutral with water
  c. Wash with 50% aqueous acetic acid
  d. Wash until neutral with water.

1.0 Gram of methyl L-tyrosyl-D-methionylglycyl-L-phenylalanyl-3-amino-1-adamantanecarboxylate hydrochloride in 100 ml of water is passed through this column at a rate of 1.0 ml/min. and the column is washed with an additional 100 ml of water. The combined eluates are lyophilized to give the acetate salt, methyl L-tyrosyl-D-methionyl-glycyl-L-phenylalanyl-3-amino-1-adamantanecarboxylate acetic acid salt.

When the above procedure is repeated with the resin in the hydroxide form (repeat only steps a. and b. of the washing procedure) there is obtained the free base, methyl L-tyrosyl-D-methionyl-glycyl-L-phenylalanyl-3-amino-1-adamantanecarboxylate.

EXAMPLE 12

Substitution of an equivalent quantity of L-p-nitrophenylalanine or L-p-chlorophenylalanine for the L-phenylalanine of Example 1 and substantial repetition of the procedures detailed in Examples 1 through 9 provides methyl L-tyrosyl-D-methionyl-glycyl-L-p-nitrophenylalanyl-3-amino-1-adamantanecarboxylate hydrochloride or L-tyrosyl-D-methionyl-glycyl-L-p-chlorophenylanyl-3-amino-1-adamantanecarboxylate hydrochloride which are represented by the following formulas

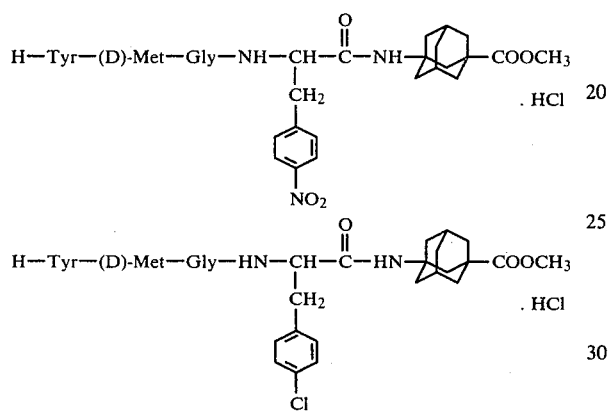

EXAMPLE 13

5.09 Grams of Boc-L-phenylalanine is dissolved in 25 ml of dry dimethylformamide and 2.13 ml of N-methylmorpholine is added. The reaction mixture is cooled to −50° C. and 2.51 ml of isobutylchloroformate is added. The reaction mixture is stirred for 15 minutes, then 1.77 ml of N-methylmorpholine and 3.93 g of methyl 3-amino-1-adamantanecarboxylate hydrochloride are added and the reaction mixture is stirred until all the methyl 3-amino-1-adamantanecarboxylate dissolves then stored for 3 days at 5° C. The reaction mixture is poured into 100 ml of water and extracted twice with 50 ml of ethyl acetate. The ethyl acetate fractions are washed twice with 50 ml of water, 50 ml of a 0.5 solution of potassium bisulfate, 50 ml of water, 50 ml of a 0.5 M solution of potassium bicarbonate, and 50 ml of water then dried over magnesium sulfate. The solvent is removed under reduced pressure, and the residue is dissolved in 150 ml of 10% chloroform in hexane and purified by low pressure chromatography on silica gel using a gradient of 10% to 50% solution of chloroform in hexane as eluent. Removal of the solvent under vacuum gives the product methyl Boc-L-phenylalanyl-3-amino-1-adamantanecarboxylate which is represented by the following formula

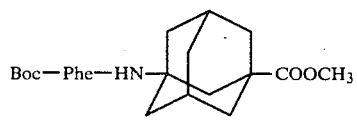

EXAMPLE 14

5.48 g of methyl Boc-phenylalanyl-3-amino-1-adamantanecarboxylate is dissolved in 15 ml of dioxane and 20 ml of a 5.9 M solution of hydrogen chloride in dioxane is added. After standing for 10 minutes at room temperature the solvent is removed under reduced pressure and the residue is stirred with diethyl ether. The crystalline product is collected by filtration, washed with diethyl ether and dried in a vacuum oven for 16 hours at 50° C. and 0.1 mm pressure to give methyl L-phenylalanyl-3-amino-1-adamantanecarboxylate hydrochloride which is represented by the following formula

EXAMPLE 15

To a solution of 16.0 g of methyl Boc-D-methionylglycinate in 50 ml of dioxane is added 50 ml of a solution of 5.6 M hydrogen chloride in dioxane. The reaction mixture is stirred for 30 minutes at room temperature and the solvent is removed under reduced pressure. The residue is stirred with diethyl ether to give a gum. The ether is decanted and the product dried under high vacuum to give methyl D-methionyl-glycinate hydrochloride which is represented by the following formula

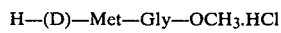

EXAMPLE 16

To a solution of 16.88 g of Boc-L-tyrosine in 50 ml of dry dimethylformamide is added 6.65 ml of N-methylmorpholine. The reaction mixture is cooled to −40° C. and 7.84 ml of isobutylchloroformate is added. The reaction mixture is allowed to warm to 0° C. over a 15 minute period then 13.32 g of methyl D-methionylglycinate hydrochloride dissolved in 50 ml of dimethylformamide is added followed immediately by 5.2 ml of N-methylmorpholine. The reaction mixture is stirred for 30 minutes at 0° C. After storage overnight at 5° C., 3 ml of N,N-dimethylethylenediamine is added and the reaction mixture is stirred for 15 minutes at room temperature. The solvent is removed under vacuum at 35° C. and 1 mm of pressure and oily residue is dissolved in a mixture of 100 ml of water and 700 ml of ethyl acetate. The ethyl acetate layer is separated and washed three times with 80 ml of a 0.5 M solution of potassium bisulfate, 2 times with 80 ml of water, 2 times with 80 ml of a 0.5 solution of potassium carbonate, and 3 times with 100 ml of a 10% solution of sodium sulfate then dried over magnesium sulfate. The solvent is removed under pressure. The residue is dissolved in 1.2 liters of 5% ethyl acetate in chloroform and purified by low pressure chromatography on silica gel then reduced to dryness under reduced pressure and recrystallized from ethyl acetate to give methyl Boc-L-tyrosyl-D-methionyl-glycinate which is represented by the following formula

EXAMPLE 17

6.02 Grams of methyl Boc-L-tyrosyl-D-methionyl-glycinate is dissolved in 30 ml of methyl alcohol and water is added until the solution becomes cloudy. A 4 M solution of potassium hydroxide is added to maintain the pH at 12-13. When the pH is stable at 13 for 30 minutes, the methanol is removed under reduced pressure. The aqueous solution is filtered and adjusted to pH 3 with concentrated hydrochloric acid. The product crystallizes and is removed by filtration and washed with water to give Boc-L-tyrosyl-D-methionyl-glycine which is represented by the following formula

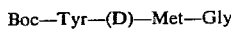

Boc—Tyr—(D)—Met—Gly

EXAMPLE 18

5.06 Grams of Boc-L-tyrosyl-D-methionyl-glycine is dissolved in 40 ml of dimethylformamide and 1.28 ml of N-methylmorpholine is added to the solution. The reaction mixture is cooled to −50° C. and 1.51 ml of isobutylchloroformate is added causing a precipitate to form. The reaction mixture is allowed to warm to −20° over a 15 minute period and 4.45 g of methyl L-phenylalanyl-3-amino-1-adamantanecarboxylate hydrochloride is added followed immediately by 1.25 ml of N-methylmorpholine The gum which forms dissolves in about 45 minutes while warming to room temperature. The reaction mixture is allowed to stand for 1.5 hours at room temperature and is then stored at 5° C. for 3 days. The reaction mixture is warmed to room temperature, 1.0 ml of N,N-dimethylethylenediamine is added and the reaction mixture is stirred for 10 minutes. The dimethylformamide is removed under reduced pressure at 32° C. and the residue is dissolved in a mixture of 70 ml of water and 100 ml of ethyl acetate. The aqueous layer is separated and extracted once with ethyl acetate and the combined ethyl acetate solutions are washed three times with 70 ml of a 0.5 M solution of potassium bisulfate, once with 70 ml of water, two times with a 0.5 M solution of potassium carbonate, and three times with 70 ml of a 10% sodium sulfate solution, then dried over magnesium sulfate. The solvent is removed under reduced pressure to give the crude product which is then purified by low pressure chromatography on silica gel to give methyl Boc-L-tyrosyl-D-methionyl-glycyl-L-phenylalanyl-3-amino-1-adamantanecarboxylate which is represented by the following formula

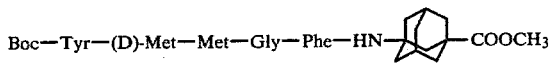

Boc—Tyr—(D)-Met—Met—Gly—Phe—HN—⟨⟩—COOCH₃

EXAMPLE 19

To a solution of 1.1 g of methyl Boc-L-tyrosylmethionyl-glycyl-L-phenylalanyl-3-amino-1-adamantanecarboxylate in 10 ml of methanol is added 10 ml of water. The pH is adjusted to 13.0 with a 4 M solution of potassium hydroxide and held at pH 13-13.5 for 2.5 hours. The pH is adjusted to 11.0 with 12 N hydrochloric acid, and the methanol is removed under vacuum. The residual aqueous solution is adjusted to pH 2.0 by the slow addition of hydrochloric acid causing the product to crystallize. The product is collected by filtration and washed with water then dried for two hours at 50° C. and 0.1 mm of pressure. The residue is dissolved in a 6 N solution of ammonia. The excess ammonia is removed under vacuum and the remaining aqueous solution is adjusted to pH 4.0 with 1 N acetic acid. The product crystallizes and is collected by filtration, washed with water and dried for 16 hours at 50° C. and 0.1 mm pressure to give Boc-L-tyrosyl-D-methionyl-glycyl-L-phenylalanyl-3-amino-1-adamantanecarboxylic acid which is represented by the following formula

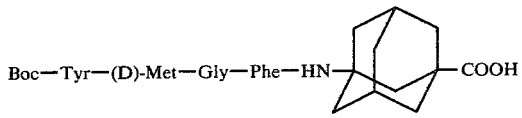

Boc—Tyr—(D)-Met—Gly—Phe—HN—⟨⟩—COOH

To a solution of 0.94 g of Boc-L-tyrosyl-D-methionyl-glycyl-L-phenyalanyl-3-amino-1-adamantanecarboxylic acid in 20 ml of dioxane is added 10 ml of a 5.7 N solution of hydrogen chloride in dioxane. The reaction mixture is allowed to stand for 30 minutes at room temperature. The solvent is removed under vacuum and the residue is dissolved in water. The cloudy solution is stirred with a small amount of SupercelHyflo for 30 minutes then filtered and lyophilized to give a white powder. The powder is dried for 2 hours at 50° C. and 0.1 mm pressure to give L-tyrosyl-D-methionyl-glycyl-L-phenylalanyl-3-amino-1-adamantanecarboxylic acid hydrochloride which is represented by the following formula

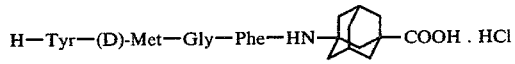

H—Tyr—(D)-Met—Gly—Phe—HN—⟨⟩—COOH . HCl

EXAMPLE 20

A solution of 0.266 g of ammonia in 9.007 g of dimethylformamide is prepared and stored in a tightly closed container until use. A solution of 1.434 g of Boc-L-tyrosyl-D-methionyl-glycyl-L-phenylalanyl-3-amino-1-adamantanecarboxylic acid in 10 ml of dimethylformamide is prepared, and to it is added 0.200 ml of N-methylmorpholine. The reaction mixture is cooled to −60° C. and 0.237 ml of isobutylchloroformate is added. The reaction mixture is stirred and allowed to warm to −10° C. over a 20 minute period, then two successive 1.04 g portions of the solution of ammonia in dimethylformamide are added and the reaction mixture is stored 2.5 hours at 0° C. Another 1.04 g of the ammonia solution is added, and the reaction mixture is stored for 1.0 hour at 0° C. The dimethylformamide is removed by distillation at 35° C. The residue is taken up in water and ethyl acetate. The ethyl acetate fraction is separated and washed twice with a 0.5 M solution of potassium carbonate, and twice with water then dried over magnesium sulfate. The solvent is removed by distillation and the residue is dried under reduced pressure to give Boc-L-tyrosyl-D-methionyl-glycyl-L-phenylalanyl-3-amino-1-adamantanecarboxamide which is represented by the following formula

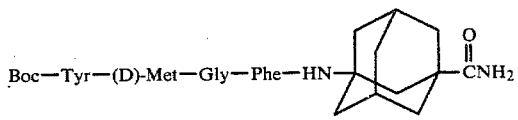

Boc—Tyr—(D)-Met—Gly—Phe—HN—⟨⟩—CNH₂

To a solution of 1.0 g of Boc-L-tyrosyl-D-methionyl-glycyl-L-phenylalanyl-3-amino-1-adamantanecarboxamide in 5.0 ml of glacial acetic acid is added 5.0 ml of a 6 N solution of hydrogen chloride in dioxane. The reaction mixture is stirred for 20 minutes at room temperature. The solvent is removed under reduced pressure, and the residue is dissolved in 125 ml of water. The solution is lyophilized to give L-tyrosyl-D-methionyl-glycyl-L-phenylalanyl-3-amino-1-adamantanecarboxamide hydrochloride which is represented by the following formula

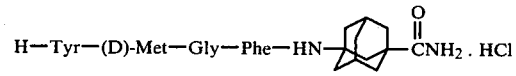

EXAMPLE 21

A solution of 14.05 g of Boc-L-tyrosine and 5.55 ml of N-methylmorpholine in 150 ml of tetrahydrofuran dried over 5A sieves is stirred under nitrogen and cooled to −50° C. To the cooled solution is added 6.5 ml of isobutylchloroformate. Over a 30 minute period the solution is warmed to −10° C. then re-cooled to −40° C. and 6.65 g of L-threonine methyl ester is added. The reaction is allowed to proceed at room temperature overnight. The solvent is removed under vacuum and the residue is partitioned between 100 ml ethyl acetate and successively 20 ml portions of cold 0.5 M potassium bisulfate, saturated sodium bicarbonate, and saturated sodium chloride solution then dried over sodium sulfate. The solution is filtered, and the solvent is removed to give Boc-L-tyrosyl-L-threonine methyl ester.

EXAMPLE 22

19.6 Grams of Boc-L-tyrosyl-L-threonine methyl ester are dissolved in 75 ml of 2 M potassium hydroxide solution at room temperature. After 30 minutes the aqueous solution is extracted with 20 ml of ethyl acetate, acidified with cold 1 M potassium bisulfate, and extracted with four 25 ml portions of ethyl acetate. The combined extracts are washed with saturated sodium chloride solution, dried over sodium sulfate and filtered. The solvent is removed under reduced pressure to give Boc-L-tyrosyl-L-threonine.

EXAMPLE 23

A. An unsaturated azlactone intermediate is prepared by stirring 3.82 g of Boc-L-tyrosyl-L-threonine with 0.82 g of anhydrous sodium acetate and 5.67 ml of acetic anhydride under a nitrogen atmosphere at room temperature overnight. The solvent is removed under reduced pressure at 40° C. and, the residue is triturated with hexane. The hexane is decanted and the residue is dried under reduced pressure over potassium hydroxide pellets. The residue is suspended in 20 ml chloroform and further dried by adding sieves (5A). The solution is filtered and combined with a solution of 5 g of methyl glycinate in 100 ml of chloroform. The volume is concentrated to about 50 ml under reduced pressure and the reaction mixture is allowed to stand overnight at room temperature. The reaction mixture is diluted with 50 ml of chloroform and washed with 20 ml portitons of cold 1 M potassium bisulfate solution, 2 M potassium carbonate solution and saturated sodium chloride solution. The reaction mixture is dried over sodium sulfate, filtered, and concentrated under reduced pressure to give the desired unsaturated tripeptide ester as a mixture of methyl Boc-tyrosyl-dehydro-α-aminobutyryl-glycinate and methyl Boc-O-acetyltyrosyl-dehydro-α-aminobutyryl glycinate. This tripeptide ester may be purified by chromatography on silica gel to give methyl Boc-O-acetyltyrosyl-dehydro-α-aminobutyryl-glycinate glycine methyl ester which is represented by the following formula

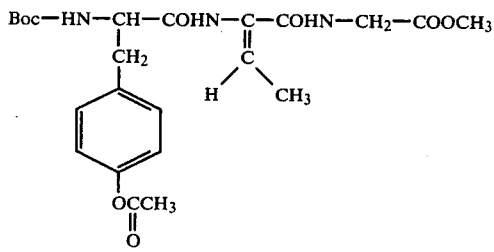

B. Under a nitrogen atmosphere the tripeptide ester from A. is dissolved in 30 ml of 1 N potassium hydroxide solution and kept at room temperature for two hours. After acidification with 3.0 ml of glacial acetic acid the reaction mixture is extracted with one 20 ml portion of chloroform and four 25 ml portions of ethyl acetate. The combined organic layers are washed with 20 ml of saturated sodium chloride solution, dried over sodium sulfate, filtered, and concentrated under reduced pressure to give the unsaturated tripeptide acid, Boc-L-tyrosyl-dehydro-α-aminobutyryl-glycine which is represented by the following formula

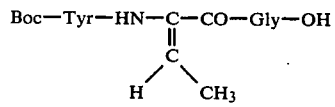

EXAMPLE 24

Under a nitrogen atmosphere 6.5 ml of isobutylchloroformate is added to 100 ml of a stirred methylene chloride solution containing 2 g of 5A sieves, 13.26 g Boc-phenylalanine, and 5.5 ml of N-methylmorpholine at −50° C. Over a 30 minute period the reaction mixture is warmed to −10° C. and then recooled to −40° C., and 7.94 g of 1-aminoadamantane is added. The cooling bath is removed, and the reaction mixture is stirred at room temperature overnight. The solution is filtered and washed with 50 ml of cold 1 M potassium bisulfate solution followed by washes with 20 ml portions of 2 M potassium carbonate solution and saturated sodium chloride solution. The solution is then dried over sodium sulfate, filtered and concentrated to dryness to give Boc-L-phenylalanyl-1-aminoadamantane which is represented by the following formula

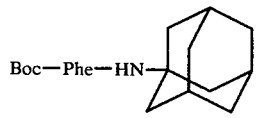

EXAMPLE 25

Under a nitrogen atmosphere a solution of 9.5 g of Boc-L-phenylalanyl-1-aminoadamantane in 25 ml of cold, dry dichloromethane is diluted with 25 ml of trifluoroacetic acid. The reaction is allowed to proceed for 45 minutes then the solution is concentrated and 50 ml of methylene chloride is added. The solution is washed with 25 ml portions of ice cold water, 2 M potassium carbonate solution, and saturated sodium chloride solution then dried over sodium sulfate, filtered and concentrated under reduced pressure. The residue is rubbed with ethyl ether and the solid isolated and dried over potassium hydroxide under reduced pressure to give L-phenylalanyl-1-aminoadamantane which is represented by the following formula

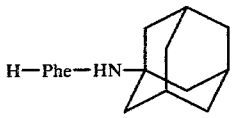

EXAMPLE 26

A dried (sieves) solution of 4.21 g of Boc-L-tyrosyl-dehydro-α-aminobutylryl-glycine and 1.11 ml of N-methylmorpholine in 20 ml of tetrahydrofuran is stirred under nitrogen and cooled to −50° C. To this solution is added 1.30 ml of isobutylchloroformate. Over a 30 minute period, the reaction mixture is warmed to −10° C. and then cooled to −40° C. at which time 3.13 g of dry L-phenylalanyl-1-aminoadamantane is added. The cooling bath is removed and the reaction mixture is stirred overnight at room temperature then filtered and washed with tetrahydrofuran. The combined filtrates are evaporated under reduced pressure and the residue is dissolved in 50 ml of methylene chloride and washed successively with 20 ml portions of saturated sodium bicarbonate, cold 1 M potassium bisulfate and saturated sodium chloride solution then dried over sodium sulfate. The dried solution is then filtered and concentrated under vacuum and purified by chromatography on silica gel in a chloroform-methanol gradient to give Boc-L-tyrosyl-dehydro-α-aminobutyryl-glycyl-L-phenylalanyl-1-aminoadamantane. Under a nitrogen atmosphere a solution of 3.51 g of this product in 10 ml of glacial acetic acid is diluted with 10 ml of 5 N solution of hydrogen chloride in dioxane. The reaction is allowed to proceed for 1 hour then the solvent is removed under reduced pressure. The residue is lyophilized to give L-tyrosyl-dehydro-α-aminobutyryl-glycyl-L-phenylalanyl-1-aminoadamantane hydrochloride which is represented by the following formula

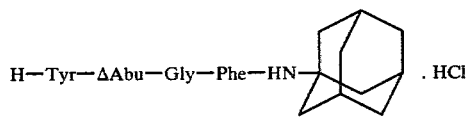

EXAMPLE 27

To a cold, dry solution of 26.3 g of Boc-methionine in 20 ml of methylene chloride under nitrogen is added dropwise with stirring 16.4 g of methyl trifluoromethanesulfonate. The solution is filtered and added to 200 ml of vigorously stirred diethyl ether. The solid is collected, resuspended in diethyl ether, and collected again then dried over potassium hydroxide under reduced pressure to give the sulfonium salt, Boc-S-methylmethionine trifluoromethanesulfonate. Using specially dried equipment, a dry solution of 17 g of the above sulfonium salt and 14.34 g of dried calcium carbonate in 40 ml of dimethylformamide which has been dried over sieves is heated to 60°–70° C. under a nitrogen atmosphere for four hours. Most of the dimethylformamide is removed under reduced pressure. The residue is acidified with 50 ml of 2 N acetic acid and the solution is extracted with 50 ml portions of ethyl acetate. The combined ethyl acetate layers are washed successively with 20 ml portions of cold 1 M potassium bisulfate solution, saturated sodium bicarbonate solution, and saturated sodium chloride solution, then dried over sodium sulfate. The solvent is removed under reduced pressure, and the residue is purified by chromatography on silica gel. The product, methyl Boc-1-aminocyclopropane-1-carboxylate is obtained from the 50% hexane-chloroform fractions as a crystalline material melting at about 80° C. and is represented by the following formula

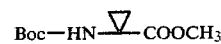

EXAMPLE 28

A solution of 3.91 g of methyl Boc-1-aminocyclopropane-1-carboxylate in 15 ml of methylene chloride is dried over sieves and filtered. 10 ml of trifluoroacetic acid is added and the reaction is allowed to proceed for 20 minutes. The solution is concentrated under reduced pressure then diluted with ethyl ether to give methyl 1-aminocyclopropane-1-carboxylate trifluoroacetate. Under a nitrogen atmosphere a mixture of 2.29 g of this trifluoacetate salt, 10.9 grams of N-t-butoxycarbonyl-tyrosine pentachlorophenyl ester and 1.11 ml of N-methylmorpholine in 15 ml of dimethylformamide is stirred at room temperature for three days. The mixture is concentrated under reduced pressure and 100 ml of methylene chloride and 0.74 g of dimethylaminoethylamine are added. After 5 minutes the slution is extracted with two 20 ml portions of cold 2 M potassium bisulfate solution. The methylene chloride solution is dried over sodium sulfate and the solvent is removed under reduced pressure to give methyl Boc-L-tyrosyl-1-aminocyclopropane-1-carboxylate. Under a nitrogen atmosphere, 3.5 g of this ester are stirred with 10 ml of 3 M potassium hydroxide for 2 hours at room temperature. The solution is extracted with 10 ml of ethyl acetate. The aqueous layer is added to 15 ml of cold, vigorously stirred 2 M potassium bisulfate solution. A fine precipitate forms and is collected by filtration, washed with water and dried to give Boc-L-tyrosyl-1-aminocyclopropane-1-carboxylic acid which is represented by the formula

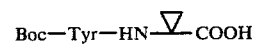

EXAMPLE 29

A solution of 1.42 g of Boc-glycine and 0.90 ml of N-methylmorpholine in 10 ml of dry methylene chloride under nitrogen is allowed to react with 1.05 ml of isobutylchloroformate at −45° C. The reaction mixture is allowed to warm to −20° C. then recooled to −40° C. To this solution is added 2.38 g of L-phenylalanyl-1-aminoadamantane. The cooling bath is removed and the reaction mixture is allowed to stand overnight at room temperature. The reaction mixture is filtered, diluted with 20 ml of methylene chloride and washed with 10 ml of cold 1 M potassium bisulfate solution followed by washing with 10 ml of cold 2 M potassium carbonate solution and 10 ml of saturated sodium chloride solution. The reaction mixture is dried over sodium sulfate, filtered and concentrated. The product separates as crystals upon addition of ether. The crystalline material is collected to give Boc-glycyl-L-phenylalanyl-1-aminoadamantane. A dry solution of 2.8 g of Boc-glycol-L-phenylalanyl-1-aminoadamantane in 15 ml of methylene chloride under a nitrogen atmosphere at 5° C. is allowed to react with 10 ml of trifluoroacetic acid. The reaction mixture is allowed to stand for 30 minutes at room temperature. The solution is concentrated under reduced pressure then diluted with 10 ml of 5 M potassium carbonate solution and extracted with methylene chloride. The reaction mixture is dried over sodium sulfate, filtered and evaporated to dryness under reduced pressure to give glycyl-L-phenylalanyl-1-aminoadamantane which is represented by the following formula

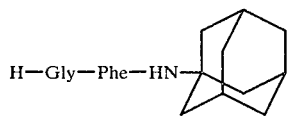

EXAMPLE 30

Under a nitrogen atmosphere a stirred suspension of dry sodium Boc-L-tyrosyl-1-amino-cyclopropane-1-carboxylate (prepared from 1.82 g of Boc-L-tyrosyl-1-aminocyclopropane-1-carboxylic acid) in 20 ml of dimethylformamide at −70° C. is allowed to react with 0.65 ml of isobutylchloroformate. Over a 30 minute period the reaction mixture is warmed to −10° C. and recooled to −40° C. To this solution is added 1.78 g of glycyl-L-phenylalanyl-1-aminoadamantane. The cooling bath is removed, and the reaction mixture is stirred at room temperature overnight, then concentrated under reduced pressure. The residue is partitioned between 20 ml of 2 M potassium carbonate and 50 ml of ethyl acetate. The organic layer is washed with 10 ml of cold 1 M potassium bisulfate solution and 10 ml of saturated sodium chloride solution, then dried over sodium sulfate, filtered and taken to dryness under reduced pressure. The residue is purified by chromatography on silica gel to give Boc-L-tyrosyl-1-aminocyclopropane-1-carboxyl-glycol-L-phenylalanyl-1-aminoadamantane. A solution of 2.80 g of this product in 5 ml of glacial acetic acid is diluted with 15 ml of a 5 N solution of hydrogen chloride in acetic acid. The reaction mixture is allowed to stand for one hour at room temperature then the solvent is removed under reduced pressure. The residue is dissolved in 20 ml of 10% aqueous acetic acid solution and lyophilized to give the hydrochloride salt, L-tyrosyl-1-aminocyclopropane-1-carboxyl-glycol-L-phenylalanyl-1-aminoadamantane hydrochloride which is represented by the following formula

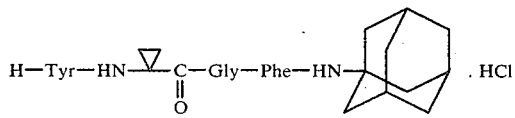

EXAMPLE 31

A solution of 1.88 g of Boc-L-tyrosyl-D-methionylglycine and 0.45 ml of N-methylmorpholine in 25 ml of dry tetrahydrofuran under nitrogen is cooled to −45° C. with stirring. To the cooled solution is added 0.52 ml of isobutylchloroformate. The reaction mixture is allowed to warm to −20° C. over a 10 minute period and is then cooled to −35° C. Following the addition of 1.9 g of L-phenylalanyl-1-aminoadamantane the reaction mixture is warmed to room temperature and allowed to stand overnight. The reaction mixture is filtered and the tetrahydrofuran is removed under reduced pressure. The residue is dissolved in methylene chloride and washed with cold 1 M potassium bisulfate solution and saturated sodium chloride solution. Removal of the solvent and purification by chromatography on silica gel gives Boc-tyrosyl-D-methionyl-glycyl-phenylalanyl-1-aminoadamantane which is represented by the following formula

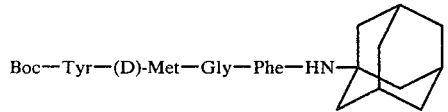

EXAMPLE 32

A solution of 1.58 of Boc-L-tyrosyl-D-methionyl-glycyl-L-phenylalanyl-1-aminoadamantane in 10 ml of dioxane is allowed to react with 30 ml of a 5 N solution of hydrochloric acid in dioxane for 1 hour. The solvent is removed under a stream of nitrogen. The residue is triturated with diethyl ether. Removal of the diethyl ether gives L-tyrosyl-D-methionyl-glycol-L-phenylalanyl-1-aminoadamantane hydrochloride which is represented by the following formula

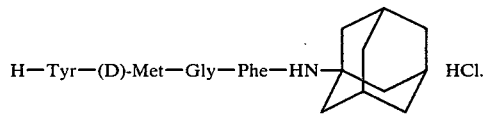

EXAMPLE 33

Substitution of an equivalent quantity of 2-aminoadamantane for the 1-aminoadamantane of Example 24 and substantial repetition of the procedures detailed in Examples 24 and 25 provides L-phenylalanyl-2-aminoadamantene. Substitution of an equivalent quantity of L-phenylalanyl-2-aminoadamantane for the L-phenylalanyl-1aminoadamantane of Example 31 and substantial repetition of the procedures detailed in Examples 31 and 32 provides L-tyrosyl-D-methionyl-glycyl-L-phenylalanyl-2-aminoadamantane hydrochloride which is represented by the following formula

EXAMPLE 34

A solution of 15.0 ml of dioxane and 15.6 ml of 4 M sodium hydroxide solution is prepared and 6.18 g of DL-2,6-dimethyltyrosine hydrochloride is dissolved in it followed by the addition of 9.23 g of 2-(t-butoxycarbonyloxyimino)-2-phenylacetonitrile. The reaction mixture is stirred for 24 hours at room temperature then diluted with 100 ml of water. The reaction mixture is extracted twice with 50 ml of ethyl acetate. The aqueous extract is adjusted to pH 2 with a 5% solution of potassium bisulfate and an oily solid is produced. The product is filtered, washed with water and dried under reduced pressure. The crude product is dissolved in chloroform:water:acetic acid:methanol (97.8:0.1:01.2.0) and purified by low pressure chromatography to give Boc-DL-2,6-dimethyltyrosine.

EXAMPLE 35

A solution of 5.34 g of Boc-DL-2,6-dimethyltyrosine and 2.0 ml of N-methylmorpholine is cooled to −20° C. The temperature is maintained at −17° C. to −20° C. while 2.4 ml of isobutylchloroformate are added dropwise. The reaction mixture is stirred for 5 minutes then a solution of 2.1 ml of N-methylmorpholine and 3.63 g of methyl D-methioninate hydrochloride in 10 ml of dimethylformamide is added while maintaining the temperature at about −20° C. The reaction mixture is stirred for 30 minutes at −20° C. then warmed to room temperature and allowed to stand overnight. The reaction mixture is added to 600 ml of a cold, 5% solution of potassium bisulfate. The gummy precipitate which forms is filtered, washed four times with 100 ml of cold water and dried under reduced pressure. Purification by low pressure chromatography on silica gel using chloroform:methanol:acetic acid:water (98:1.8:0.01) as eluent gives methyl Boc-2,6-dimethyl-DL-tyrosyl-D-methioninate.

EXAMPLE 36

To a solution of 4.27 g of methyl Boc-2,6-dimethyl-DL-tyrosyl-D-methioninate in 14 ml of methanol is added a solution of 1.18 g of lithium hydroxide hydrate in 14 ml of water. The reaction mixture is stirred for 3 hours in the cold then 100 ml of a 5% solution of potassium bisulfate is added to bring the pH to 2.5 The gummy product which forms is extracted with ethyl acetate. The ethyl acetate layers are collected and combined, then washed with water and dried over magnesium sulfate. The solution is filtered to remove the magnesium sulfate and the solvent is removed under reduced pressure to give Boc-2,6-dimethyl-DL-tyrosyl-D-methionine.

EXAMPLE 37

To a solution of 1.0 g of methyl L-phenylalanyl-3-amino-1-adamantanecarboxylate and 1.03 g of 2,4,5-trichlorophenyl Boc-glycinate in 5 ml of dimethylformamide is added 0.3 ml of N-methylmorpholine. The reaction mixture is stirred for 3.5 hours then allowed to stand overnight at room temperature. The reaction mixture is added to 75 ml of a cold, 5% aqueous solution of potassium bisulfate. The gummy precipitate which forms is extracted three times with 25 ml of ethyl acetate. The combined ethyl acetate extracts are washed with water, dried over magnesium sulfate and filtered. The solvent is removed under reduced pressure to give a glassy foam. The crude product is dissolved in chloroform and purified by low pressure chromatography on silica gel using ethyl acetate/chloroform as eluent. Removal of the solvent affords a white, crystalline product which is methyl Boc-glycol-L-phenylalanyl-3-amino-1-adamantanecarboxylate.

EXAMPLE 38

1.21 grams of methyl Boc-glycol-L-phenylalanyl-3-amino-1-adamantanecarboxylate is dissolved in 8 ml of acetic acid, and 4.0 ml of a 6.0 M solution of hydrogen chloride in dioxane is added. The reaction mixture is allowed to stand for 15 minutes at room temperature and the solvents are removed under reduced pressure. Addition of diethyl ether to the residue gives a white precipitate which is collected by filtration, washed with diethyl ether and dried under reduced pressure at 60° C. for 2.5 hours to give methyl glycyl-L-phenylalanyl-3-amino-1-adamantanecarboxylate hydrochloride.

EXAMPLE 39

Substitution of equivalent quantities of Boc-2,6-dimethyl-DL-tyrosyl-D-methionine and methyl glycyl-L-phenylalanyl-3-amino-1-adamantanecarboxylate hydrochloride for the Boc-2,6-diemthyl-DL-tyrosine and methyl D-methioninate hydrochloride respectively of Example 35 and substantial repetition of the procedures described therein affords methyl Boc-2,6-dimethyl-DL-tyrosyl-D-methionyl-glycyl-L-phenylalanyl-3-amino-1-adamantanecarboxylate. When this compound is substituted for the methyl Boc-glycyl-L-phenylalanyl-3-amino-1-adamantanecarboxylate of Example 38 and the procedures described therein substantially repeated there is obtained methyl 2,6-dimethyl-DL-tyrosyl-D-methionyl-glycyl-L-phenylalanyl-3-amino-1-adamantanecarboxylate hydrochloride which is represented by the following formula

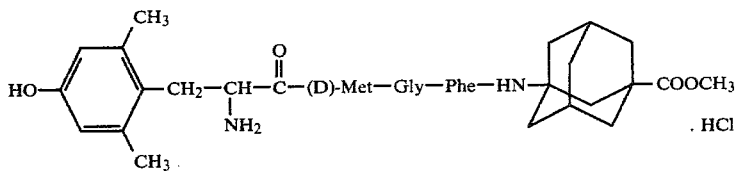

EXAMPLE 40

Substitution of Boc-$\beta,\beta$-dimethyl-DL-tyrosine for the Boc-2,6-dimethyl-DL-tyrosine of Example 34 and substantial repetition of the procedures described in Examples 34, 35, 36, 37 and 39 affords two diastereoisomers which are separated by low pressure chromatography on silica gel eluting with a gradient of chloroform:Skelly B:methanol (85:5:0.5) to methanol:chloroform (5:95) to afford methyl Boc-$\beta,\beta$-dimethyltyrosyl-D-methionyl-glycyl-L-phenylalanyl-3-amino-L-adamantanecarboxylate (Isomer I), $R_f$=0.48 in 5% methanol—95% chloroform and methyl Boc-$\beta,\beta$-dimethyltyrosyl-D-methionyl-glycyl-L-phenylalanyl-3- amino-1-adamantanecarboxylate (Isomer II), $R_f=0.37$ in 5% methanol=95% chloroform.

These isomeric products are deblocked according to the procedure described in Example 38. The compounds are dissolved in acetic acid then allowed to react with a 6 M solution of hydrogen chloride in dioxane for 15 minutes at room temperature. The solvents are removed under reduced pressure and diethyl ether is added. The resulting precipitates are collected by filtration, washed with diethyl ether and dried under reduced pressure to give methyl $\beta,\beta$-dimethyltyrosyl-D-methionyl-glycyl-L-phenylalanyl-3-amino-1-adamantanecarboxylate hydrochloride (Isomer I) $[\alpha]_D^{25} -14°$ (c 1, acetic acid) and methyl $\beta,\beta$-dimethyltyrosyl-D-methionyl-glycyl-L-phenylalanyl-3-amino-1-adamantanecarboxylate hydrochloride (Isomer II) $[\alpha]_D^{25} +19.5°$ (c 1, acetic acid) which are represented by the following formula justed to pH 3 with a 1 M solution of potassium bisulfate. The resulting precipitate is collected by filtration, washed with water and dried to give Boc-L-tyrosyl-D-alanylglycine.

EXAMPLE 45

Substitution of Boc-L-tyrosyl-D-alanylglycine and methyl L-phenylalanyl-3-amino-1-adamantanecarboxylate hydrochloride for the Boc-D-alanine and methyl glycinate hydrochloride respectively of Example 41 and substantial repetition of the procedures described therein provides methyl Boc-L-tyrosyl-D-alanylglycyl-L-phenylalanyl-3-amino-1-adamantanecarboxylate.

EXAMPLE 46

Substitution of methyl Boc-L-tyrosyl-D-alanylglycyl-L-phenylalanyl-3-amino-1-adamantanecarboxylate for the methyl Boc-D-alanylglycinate of Example 42

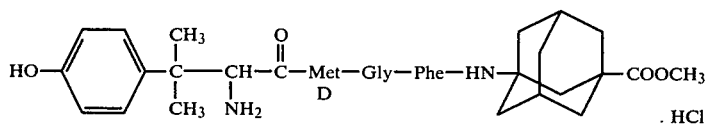

EXAMPLE 41

18.9 Grams of Boc-D-alanine are dissolved in 100 ml of methylene chloride, and 22.0 ml of N-methylmorpholine is added. The solution is cooled to $-70°$ C. and 13.0 ml of isobutylchloroformate is added. The reaction mixture is warmed to $-15°$ C. and again cooled to $-70°$ C. and 12.6 g of methyl glycinate hydrochloride is added. The reaction mixture is stirred for sixteen hours at room temperature then extracted three times with a 1.0 M solution of potassium bisulfate, saturated potassium bicarbonate solution, and a saturated sodium chloride solution. The methylene chloride solution is dried over anhydrous sodium sulfate, filtered and stripped of solvent. The product is purified by chromatography on silica gel using methanol-chloroform eluant. Removal of the solvent provides methyl Boc-D-alanylglycinate.

EXAMPLE 42

26.0 Grams of methyl Boc-D-alanylglycinate is dissolved in 340 ml of acetic acid, and 170 ml of a 6 N solution of hydrogen chloride in dioxane is added to the solution. The reaction mixture is allowed to stand for ten minutes and then the solvent is removed under vacuum. The residue is triturated with diethyl ether. The resulting white precipitate is filtered and washed with diethyl ether to afford methyl-D-alanylglycinate hydrochloride.

EXAMPLE 43

If Boc-L-tyrosine and methyl-D-alanylglycinate hydrochloride are substituted for the Boc-D-alanine and methyl glycinate hydrochloride respectively of Example 41 and the procedures described therein are substantially repeated there is obtained methyl Boc-L-tyrosyl-D-alanylglycinate.

EXAMPLE 44

42.3 Grams of methyl Boc-L-tyrosyl-D-alanylglycinate is dissolved in 200 ml of methanol and 200 ml of a 1 N solution of sodium hydroxide is added. The reaction mixture is allowed to stand for 30 minutes, then is adand substantial repetition of the procedures described therein provides methyl L-tyrosyl-D-alanyl-glycyl-L-phenylalanyl-3-amino-1-adamantanecarboxylate hydrochloride which is represented by the following formula

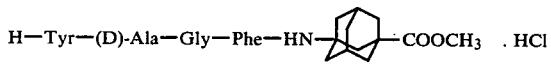

EXAMPLE 47

To a solution of 100 ml of 2-hydroxyadamantane dissolved in 250 ml pyridine is added 137.9 g of trifluoroacetic anhydride dropwise, and the reaction mixture is stirred overnight. The reaction mixture is poured over ice then diluted to 1.0 liter with water and extracted three times with 500 ml of diethyl ether. The combined diethyl ether extracts are washed with 5% hydrochloric acid until the wash is acidic then washed once with 5% sodium bicarbonate solution and dried over magnesium sulfate. The solvent is removed under reduced pressure to give 2-adamantyl trifluoroacetate as an oil. 50 Grams of 2-adamantyl trifluoroacetate are dissoled in 500 ml of hexane and photolyzed (254 nm) for 4 days. The solvent is removed under reduced pressure and the oily residue is placed in a low pressure column and eluted with dichloroethane. The starting material is the first major component eluted. The second major component is the product, 1-trifluoroacetyl-2-hydroxyadamantane which is crystallized from pentane. To 100 ml of 10% sodium hydroxide solution is added 13.0 g of 1-trifluoroacetyl-2-hydroxyadamantane. The reaction mixture is heated for 15 minutes on a steam bath then diluted to 200 ml with water and washed two times with 150 ml of diethyl ether. The aqueous solution is acidified with concentrated hydrochloric acid. The precipitate is collected by filtration, washed with water and dried in a steam cabinet to give 2-hydroxy-1-adamantanecarboxylic acid. 6.7 Grams of 2-hydroxy-1-adamantanecarboxylic acid are dissolved in 50 ml of acetone and enough 8 N Jones Reagent (chromic anhydride in dilute sulfuric acid) is added to retain a red color for 1 minute. Isopropyl alconhol is added to destroy any excess Jones reagent and the solvent is removed under reduced pressure. The residue is diluted with water, collected by filtration and washed with water then suction dried to give 2-keto-1-adamantanecarboxylic acid. 4.7 Grams of 2-keto-1-adamantanecarboxylic acid is dissolved in 75 ml of ethanol and hydrogenated over platinum oxide in the presence of ammonia gas under 60 psi of pressure at room temperature. The solvent is removed under reduced pressure. 15 ml of water is added to the residue and removed under reduced pressure. This step is repeated with another 15 ml of water then the residue is dried at 100° C. under reduced pressure for 1 hour to give 2-amino-1-adamantanecarboxylic acid which is represented by the following structure

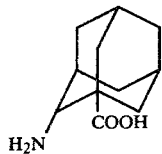

EXAMPLE 48

To a stirred solution of 4.4 g of 2-amino-1-adamantanecarboxylic acid in 100 ml of dry methanol at −70° C. is added 3.21 ml of thionyl chloride. The reaction mixture is allowed to stand at room temperature overnight. Removal of the solvent under reduced pressure gives methyl-2-amino-1-adamantanecarboxylate hydrochloride which is represented by the formula

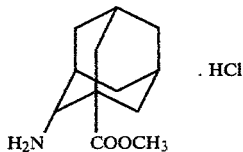

The residue containing the methyl 2-amino-1-adamantanecarboxylate hydrochloride is dissolved in 150 ml of chloroform, filtered through Filter Cel, washed with 10 ml of 5 M potassium carbonate solution, separated and then combined with a second chloroform extract of the aqueous phase. The chloroform extract is dried over sodium sulfate, filtered through Filter Cel and concentrated en vacuo. The syrup-like residue is dissolved in 10 ml of tetrahydrofuran and dried over sieves for 30 minutes before used in the mixed anhydride reaction. A dry (sieves) solution of 6.37 g of Boc-L-phenylalanine and 2.66 ml of N-methylmorpholine is stirred under a nitrogen atmosphere at −60° C. To this solution is added 2.12 ml of isobutylchloroformate. The solution is allowed to warm to −10° C. then is cooled to −40° C. over a 10 minute time period, and the tetrahydrofuran solution of methyl 2-amino-1-adamantane-carboxylate from above is added. The reaction mixture is warmed to room temperature and stirred overnight. 150 ml of chloroform is added and the chloroform solution is washed twice with 10 ml of 2 M potassium carbonate solution and once with 20 ml of 1 M potassium bisulfate solution. The chloroform layer is collected, dried over sodium sulfate and concentrated under reduced pressure to give an oily residue. Thin layer chromatography using 2.5% methanol-chloroform as eluent and NMR (CDCl$_3$, 60 MHz, tetramethylsilane internal standard) on the oily residue indicates two disastereoisomers, A and B, of methyl Boc-L-phenylalanyl-2-amino-1-adamantanecarboxylate. Isomer A (Rf=0.41, —CO$_2$Me at 216 cps) is obtained from ether as a crystalline solid melting at 153°–158° C. Isomer B (Rf=0.46, —CO$_2$Me at 212 cps) and additional Isomer A are obtained by chromatographic separation on silica gel using a hexane-chloroform gradient.

A. To a solution of 1.862 g of methyl Boc-L-phenylalanyl-2-amino-1-adamantanecarboxylate (Isomer A) in 10 ml of methylene chloride is added 5 ml of trifluoracetic acid. After 15 minutes at room temperature the reaction mixture is concentrated to a small volume and 5 ml of cold potassium carbonate is added. The mixture is extracted twice with 20 ml of chloroform. The combined chloroform extracts are dried over sodium sulfate to give methyl L-phenylalanyl-2-amino-1-adamantanecarboxylate (Isomer A) as a crystalline solid melting at 160°–167° C. Under a nitrogen atmosphere at −50° C. a dry (1 g of 4 A sieves) solution of 1.878 g of Boc-L-tyrosyl-D-methionyl-glycine and 0.444 ml of N-methylmorpholine in 25 ml of tetrahydrofuran is stirred while 0.52 ml of isobutylchloroformate is added. The reaction mixture is allowed to warm to −10° C. for 10 minutes then cooled to −40° C. and 1.24 g of methyl L-phenylalanyl-2-amino-1-adamantanecarboxylate is added. The reaction mixture is stirred overnight at room temperature. Upon the addition of water a solid separates and is collected by filtration, washed and dried. The residue is dissolved in methanol, filtered through Filter Cel, concentrated and diluted with equal volumes of ethyl acetate and ether. The solid which precipitates is collected by filtration, washed with ether and dried to give methyl Boc-L-tyrosyl-D-methionyl-glycyl-L-phenylalanyl-2-amino-1-adamantanecarboxylate (Isomer A). 2.34 Grams of this compound is dissolved in 10 ml of acetic acid and 20 ml of a 5 N solution of hydrogen chloride in dioxane is added. The reaction mixture is concentrated under a stream of nitrogen for 1½ hours and diluted with 150 ml of ether. The solid which forms is collected, dissolved in methanol, concentrated to about 10 ml and diluted with 40 ml of water then allowed to stand overnight at room temperature. The solution is filtered and lyophilized to give methyl L-tyrosyl-D-methionyl-glycyl-L-phenylalanyl-2-amino-1-adamantanecarboxylate hydrochloride (Isomer A) which is represented by the following formula

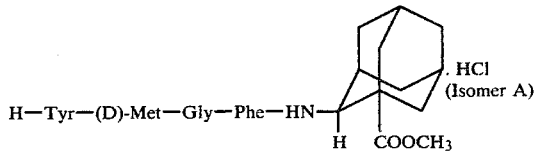

B. To a solution of 1.7 g of methyl Boc-L-phenylalanyl-2-amino-1-adamantanecarboxylate (Isomer B) in 10 ml of methylene chloride is added 5 ml of trifluoroacetic acid. After 15 minutes the reaction mixture is concentrated to a small volume under a stream of nitrogen then distributed between 25 ml of methylene chloride and 5 ml of 5 M potassium carbonate solution. The methylene chloride layer is collected and the aqueous phase is extracted with another 25 ml of methylene chloride. The methylene chloride extracts are combined, dried over sodium sulfate and concentrated to a small volume, then diluted with hexane. The crystalline product which forms is collected by filtration to give methyl L-phenylalanyl-2-amino-1-adamantanecarboxylate (Isomer B) melting at 88°-90° C. The mixed anhydride from 1.65 g of Boc-L-tyrosyl-D-methionylglycine is prepared as in Part A above. To it is added 1.256 g of methyl L-phenylalanyl-2-amino-1-adamantanecarboxylate (Isomer B). The reaction is allowed to proceed for 1 hour at room temperature then 50 ml of methylene chloride is added. The reaction mixture is filtered, washed with 10 ml portions of 2 M potassium carbonate solution and 1 M potassium bisulfate solution, dried over sodium sulfate, and filtered. The solvent is removed under vacuum to give a glass which is methyl Boc-L-tyrosyl-D-methionyl-glycyl-L-phenylalanyl-2-amino-1-adamantanecarboxylate. This product is dissolved in 10 ml of glacial acetic acid and 20 ml of a 5 N solution of hydrogen chloride in dioxane is added. The reaction is allowed to proceed for 45 minutes, then the reaction mixture is concentrated under reduced pressure. The residue is dissolved in aqueous methanol and filtered through Filter Cel, then extracted with six 10 ml portions of methylene chloride and ethyl acetate. The ethyl acetate extracts are combined and the solvent is removed by evaporation. The residue is dissolved in 40 ml of water, filtered through Filter Cel and lyophilized to give the product methyl L-tyrosyl-D-methionyl-glycyl-L-phenylalanyl 2-amino-1-adamantanecarboxylate hydrochloride which is represented by the following formula

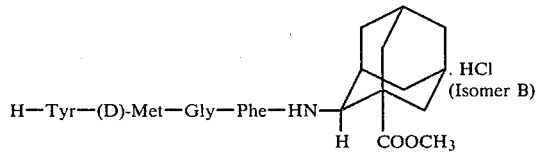

EXAMPLE 49

A. To a solution of 0.798 g of methyl L-tyrosyl-D-methionyl-glycyl-L-phenylalanyl-2-amino-1-adamantanecarboxylate hydrochloride (Isomer A) in 10 ml of 10% aqueous methanol is added 2 ml of 30% hydrogen peroxide solution. The reaction mixture is concentrated under reduced pressure and the residue is dissolved in water and lyophilized to give methyl L-tyrosyl-D-methionyl-glycyl-L-phenylalanyl-2 -amino-1-adamantanecarboxylate sulfoxide hydrochloride which is represented by the following formula

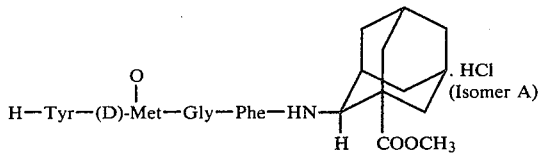

B. Substitution of an equivalent quantity if Isomer B of methyl L-tyrosyl-D-methionyl-glycyl-L-phenylalanyl-2-amino-1-adamantanecarboxylate hydrochloride for the Isomer A of Part A and substantial repetition of the procedures described therein gives methyl L-tyrosyl-D-methionyl-glycyl-L-phenylalanyl-2-amino-1-adamantanecarboxylate sulfoxide hydrochloride which is represented by the following formula

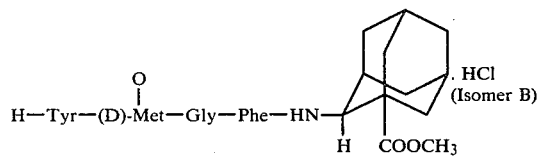

EXAMPLE 50

A solution of 13.3 g of O-methyl homoserine in 370 ml of methanol and 180 ml of a 6 N solution of hydrogen chloride in dioxane is allowed to stand at room temperature for 3 to 4 days. The solvent is removed under reduced pressure and the residue lyophilized to give O-methyl homoserine methyl ester hydrochloride which is represented by the following formula

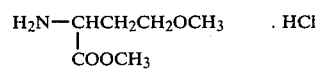

Substitution of an equivalent quantity of O-methyl homoserine methyl ester hydrochloride for the methyl D-methioninate hydrochloride of Example 35 and substantial repetition of the procedures described in Examples 35 through 39 provides methyl DL-2,6-dimethyl-tyrosyl-DL-O-methylhomoseryl-glycyl-L-phenylalanyl-3-amino-1-adamantanecarboxylate hydrochloride which is represented by the following formula

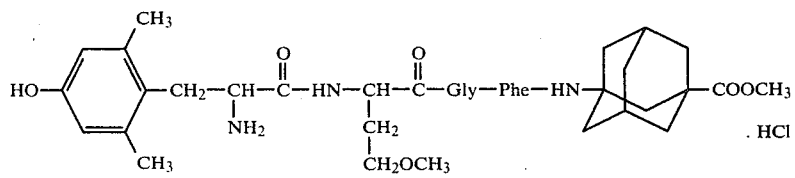

EXAMPLE 51

To a solution of 13.7 g of thionyl chloride in 100 ml of methanol at −20° C. is added 5 g of D-norleucine (Nle) with stirring. The reaction mixture is allowed to stand for 16 hours at room temperature. The methanol is removed under reduced pressure and the residue is shaken with diethyl ether to give a crystalline product, methyl D-norleucinate hydrochloride which is represented by the folowing formula

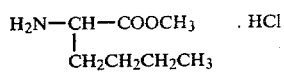

A solution of 12.4 g of Boc-L-tyrosine in 100 ml of dimethylformamide is cooled to −20° C. and converted to a mixed anhydride by the addition of 1 equivalent of N-methyl morpholine and 1 equivalent of isobutylchloroformate. The reaction mixture is cooled to −30° C. and 4.48 ml of N-methylmorpholine is added followed by 6.65 g of methyl D-norleucinate hydrochloride. The reaction mixture is stirred 3 hours at room temperature and allowed to stand an additional 16 hours. The dimethylformamide is distilled off under high vacuum at 40° C., and the residue is shaken with ethyl acetate and water. The ethyl acetate fraction is separated and washed successively with 0.5 M potassium bisulfate solution, water, and 1 M potassium bicarbonate solution, then dried over magnesium sulfate. The solvent is removed under reduced pressure and the product is crystallized from 50 ml of isopropanol and 40 ml of water to give methyl Boc-L-tyrosyl-D-norleucinate. 4.06 Grams of methyl Boc-L-tyrosyl-D-norleucinate is suspended in 40 ml of 1 M potassium hydroxide solution and the mixture is stirred for one hour at room temperature. Excess 2 M potassium bisulfate solution is added and the product is taken up in ethyl acetate. The ethyl acetate solution is washed successively with 0.5 M potassium bisulfate solution and water then dried over magnesium sulfate. The solvent is removed under reduced pressure to give Boc-L-tyrosyl-D-norleucine. A solution of 1.42 g of Boc-L-tyrosyl-D-norleucine in 15 ml of tetrahydrofuran is cooled to −20° C. and converted to the mixed anhydride by the addition of 1 equivalent of N-methylmorpholine and 1 equivalent of isobutylchloroformate. To this reaction is added 1.24 g of methyl glycyl-L-phenylalanyl-3-amino-1-adamantanecarboxylate. The reaction mixture is stirred for 2 hours at room temperature then allowed to stand for 16 hours at room temperature. The reaction mixture is diluted with 200 ml of ethyl acetate and the ethyl acetate solution is washed successively with 0.5 M potassisum bisulfate solution, water, and 1 M potassisum bicarbonate solution, then dried over magnesium sulfate. The solvent is removed under reduced pressure and the product is purified by low pressure chromatography on Woelm silica gel using a 100% chloroform to 5% methanol-95% chloroform gradient to give methyl Boc-L-tyrosyl-D-norleucyl-glycyl-L-phenylalanyl-3-amino-1-adamantanecarboxylate.

To a solution of 0.896 g of methyl Boc-L-tyrosyl-D-norleucyl-glycyl-phenylalanyl-3-amino-1-adamantanecarboxylate in 10 ml of methyl acetate is added 10 ml of a 6 M solution of hydrogen chloride in dioxane. The reaction mixture is allowed to stand for one hour at room temperature, then the solvent is removed under vacuum. The residue is extracted with ethyl acetate. Removal of the solvent gives methyl L-tyrosyl-D-norleucyl-glycyl-L-phenylalanyl-3-amino-1-adamantanecarboxylate hydrochloride which is represented by the formula

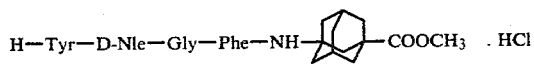

EXAMPLE 52

To 500 ml of methanol at −20° C. is added 180 ml of thionyl chloride followed by 91.3 g of β-hydroxyphenylalanine (β-OH-Phe). The reaction mixture is stirred for 24 hours at room temperature and the solvent is removed under reduced pressure. The residue is shaken with diethyl ether. Removal of the solvent gives methyl DL-β-hydroxyphenylalaninate hydrochloride which is represented by the following formula

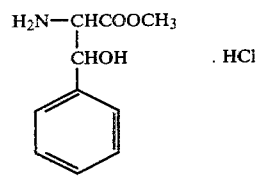

23.1 Grams of methyl DL-β-hydroxyphenylalaninate hydrochloride are finely powdered and suspended in 230 ml of methylene chloride. To the suspension is added 19.3 grams of Boc-glycine and 11.2 ml of N-methylmorpholine. The reaction mixture is stirred for 30 minutes at room temperature then cooled to 0° C., and a solution of 23.7 g of dicyclohexylcarbodiimide in 100 ml of methylene chloride is added in one portion. The mixture is stirred four hours at room temperature then filtered to remove the dicyclohexylurea which forms during the reaction. The methylene chloride filtrate is reduced to dryness under vacuum and the residue is shaken with ethyl acetate and filtered to remove N-methylmorpholine hydrochloride. The filtrate is washed successively with 0.5 M potassium bisulfate solution, water, and 1 M potassium bicarbonate solution then dried over magnesium sulfate. The solvent is removed under reduced pressure to give methyl Boc-glycyl-DL-β-hydroxyphenylalaninate. 7.03 Grams of this dipeptide is dissolved in 40 ml of dioxane and 20 ml of a 6 M solution of hydrogen chloride in dioxane is added. The reaction mixture is allowed to stand for 2 hours at room temperature, then the solvent is removed under vacuum. The residue is rubbed with diethyl ether to give a powder which is methyl glycyl-DL-β-hydroxyphenylalaninate hydrochloride. 5.17 Grams of this dipeptide and 5.23 g of Boc-D-methionine are dissolved in 20 ml of dimethylformamide and the solution is cooled to −10° C. One equivalent of N-methylmorpholine is added followed immediately by 4.32 g of dicyclohexylcarbodiimide in 20 ml methylene chloride. The reaction mixture is stirred for 4 hours at room temperature then filtered. The filtrate is diluted with 300 ml of ethyl acetate and the ethyl acetate solution is washed successively with 0.5 M potassium bisulfate solution, water, and 1 M potassium bicarbonate then dried over magnesium sulfate. The solvent is removed under reduced pressure to give a crude glass which is purified by low pressure chromatography on Woelm silica gel eluting with a gradient of 50% chloroform-50% Skelly B to 100% chloroform followed by a second gradient of 100% chloroform to 50% methanol-50% chloroform to give methyl Boc-D-methionyl-glycyl-DL-β-hydroxyphenylalaninate, 5.95 Grams of this tripeptide ester is dissolved in 50 ml of methanol. The solution is cooled to 10° C. and 50 ml of 1 M potassium hydroxide is added with stirring. The reaction is rapidly completed. To the reaction mixture is added 3.0 ml of acetic acid and the methanol is removed under reduced pressure. The residue is extracted with ethyl acetate. The ethyl acetate solution is washed with 0.5 M potassium bisulfate solution and water and dried over magnesium sulfate. The solvent is evaporated under reduced pressure to give Boc-D-methionyl-glycyl-DL-β-hydroxyphenylalanine. 4.69 Grams of this tripeptide is dissolved in 10 ml of acetic anhydride and 0.82 g of anhydrous sodium acetate is added. The reaction mixture is stirred for 16 hours at room temperature, then the reaction mixture is stirred with two 25 ml portions of Skelly B to remove most of the acetic anhydride. The Skelly B washes are discarded. The gummy residue is stirred with 25 ml of water resulting in the formation of a granular precipitate. The precipitate is collected by filtration and washed with a large volume of water to give the azlactone product, 2-Boc-D-methionylaminomethyl-4-benzylideneoxazolin-5-one which is represented by the following formula

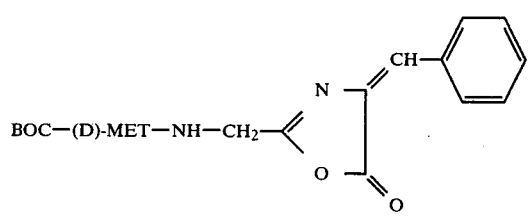

3.38 Grams of this product and 1.67 g of methyl 3-amino-1-adamantanecarboxylate are dissolved in 15 ml of ethyl acetate, and the solution is heated to 60° C. for two hours. The reaction mixture is diluted with 150 ml of ethyl acetate and the ethyl acetate solution is washed successively with 0.5 M potassium bisulfate solution, water, and 1 M potassium bicarbonate solution then dried over magnesium sulfate. The solvent is removed under reduced pressure and the residue is purified by low pressure chromatography on Woelm silica gel using a gradient of 100% chloroform to 5% methanol-95% chloroform as elutant to give methyl Boc-D-methionyl-glycyldehydrophenylalanyl-3-amino-1-adamantanecarboxylate. 3.21 Grams of this product is dissolved in 30 ml of dioxane and 30 ml of a 6 N solution of hydrogen chloride in dioxane is added. The reaction mixture is allowed to stand for one hour at room temperature then the solvent is removed under reduced pressure. The residue is shaken with diethyl ether. Removal of the solvent yields a power which is methyl D-methionyl-glycyl-dehydrophenylalanyl-3-amino-1-adamantanecarboxylate hydrochloride. A mixed anhydride is prepared by adding one equivalent of N-methylmorpholine and one equivalent of isobutylchloroformate to a solution of Boc-L-tyrosine in 17 ml of dimethylformamide at −20° C. To the reaction mixture is added 2.9 g of methyl D-methionyl-glycyl-dehydrophenylalanyl-3-amino-1-adamantanecarboxylate hydrochloride and one equivalent of N-methylmorpholine. The mixture is allowed to stand overnight at room temperature. The solvent is removed under reduced pressure, and the residue is extracted with ethyl acetate. The ethyl acetate solution is washed successively with 0.5 M potassium bisulfate solution, water, and 1 M potassium bicarbonate solution then dried over magnesium sulfate. The solvent is removed under reduced pressure. The residue is purified by low pressure chromatography on Woelm silica gel eluting with a gradient of 80% chloroform-20% Skelly B to 100% chloroform followed by a second gradient of 100% chloroform to 50% methanol-50% chloroform to give methyl Boc-L-tyrosyl-D-methionyl-glycyl-dehydrophenylalanyl-3-amino-1-adamantanecarboxylate. 0.805 Gram of this protected peptide is dissolved in 10 ml of methyl acetate and 10 ml of a 6 M solution of hydrogen chloride in dioxane is added. The solution is allowed to stand for one hour at room temperature then the solvent is removed under reduced pressure. The residue is shaken with ethyl acetate to give a powder which is collected by filtration to provide methyl L-tyrosyl-D-methionyl-glycyl-dehydrophenylalanyl-3-amino-1-adamantanecarboxylate hydrochloride which is represented by the following formula

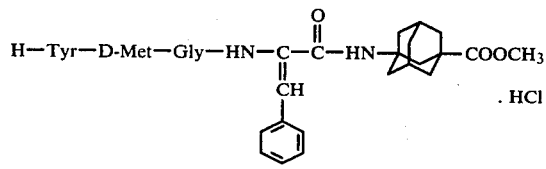

EXAMPLE 53

Boc-N-methyl-L-phenylalanine is prepared by the method of S. T. Cheung and N. L. Benoiton, CAN. J. CHEM. 55:906 (1977), and 3.35 g is dissolved in 35 ml of dimethylformamide and converted to the mixed anhydride by the addition of one equivalent of N-methylmorpholine followed by cooling to −20° C. and the addition of one equivalent of isobutylchloroformate dropwise with stirring while maintaining the temperature below −10° C. To the reaction mixture is added 2.46 g of methyl-3-amino-1-adamantanecarboxylate hydrochloride followed by 1.1 ml of N-methylmorpholine. After 24 hours at room temperature the dimethyformamide is distilled off under high vacuum. The residue is taken up in ethyl acetate and the solution is washed successively with 0.5 M potassium bisulfate, water, and 1 M potassium bicarbonate, then dried over magnesium sulfate. The solvent is removed under reduced pressure, and the crude product is purified by low pressure chromatography on Woelm silica gel using a gradient of 20% chloroform-80% Skelly B to 100% chloroform to give methyl Boc-N-methyl-L-phenylalanyl-3-amino-1-adamantanecarboxylate. 2.87 Grams of this product is dissolved in 25 ml of dioxane, 25 ml of a 6 M solution of hydrogen chloride in dioxane is added, and the solution is allowed to stand for one hour at room temperature. The solvent is removed under reduced pressure and the residue is dried under high vacuum to give methyl N-methyl-L-phenylalanyl-3-amino-1-adamantanecarboxylate hydrochloride. This product (0.006 mole) is dissolved in 10 ml of methylene chloride and 0.78 ml of N-methylmorpholine is added.

To the reaction mixture is added 1.58 g of Boc-glycine. The reaction mixture is cooled to −10° C. and 1.86 g of dicyclohexycarbodiimide in 10 ml of methylene chloride is added. After 2 hours at room temperature the mixture is filtered and the filtrate evaporated to dryness under reduced pressure. The residue is taken up in ethyl acetate and the ethyl acetate solution is washed successively with 0.5 M potassium bisulfate, water, and 1 M potassium bicarbonate and dried over magnesium sulfate. The solvent is removed under reduced pressure and the residue is purified by low pressure chromatography eluting with a gradient of 10% chloroform-90% Skelly B to 100% chloroform to give a glass which is methyl Boc-glycyl-N-methyl-L-phenylalanyl-3-amino-1-adamantanecarboxylate. 2.5 Grams of this product is dissolved in 10 ml of dioxane and 20 ml of a 6 M solution of hydrogen chloride in dioxane is added. The reaction mixture is allowed to stand for one hour at room temperature, then is evaporated to dryness under reduced pressure to give methyl glycyl-N-methyl-L-phenylalanyl-3-amino-1-adamantanecarboxylate hydrochloride which is represented by the following formula

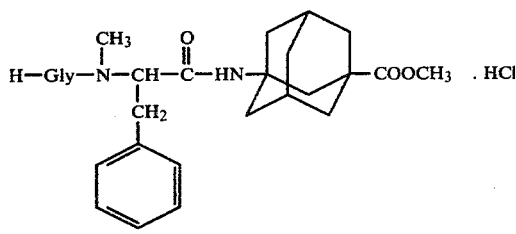

1.50 Grams of Boc-D-methionine is dissolved in 10 ml of tetrahydrofuran and converted to the mixed anhydride by the addition of one equivalent of N-methylmorpholine, cooling to −20° C., and adding one equivalent of isobutylchoroformate while maintaining a temperature below −10° C. The methyl glycyl-N-methyl-L-phenylalanyl-3-amino-1-adamantanecarboxylate hydrochloride obtained above (2.18 g) is dissolved in 10 ml of tetrahydrofuran, neutralized by the addition of 0.56 ml of N-methylmorpholine, and added to the mixed anhydride at −30° C. The reaction mixture is allowed to stand for 2 hours at room temperature, then the solvent is removed under reduced pressure and the residue is taken up in ethyl acetate. The ethyl acetate solution is washed successively with 0.5 M potassium bisulfate, water and 1 M potassium bicarbonate and dried over magnesium sulfate. The solvent is removed under reduced pressure to give methyl Boc-D-methionyl-glycyl-N-methyl-L-phenylalanyl-3-amino-1-adamantanecarboxylate. This product is deblocked by dissolving 3.0 grams of it in 20 ml of dioxane and adding 30 ml of a 6 M solution of hydrogen chloride in dioxane. The reaction mixture is allowed to stand for one hour at room temperature then the solvent is removed under reduced pressure to give methyl D-methionyl-glycyl-N-methyl-L-phenylalanyl-3-amino-1-adamantanecarboxylate hydrochloride. 1.31 Grams of this product are dissolved in 30 ml of tetrahydrofuran. To this solution is added 0.49 ml of N-methylmorpholine followed by 2.33 g of Boc-L-tyrosine-pentachlorophenyl ester. The reaction mixture is allowed to stand at room temperature, then is extracted with ethyl acetate. The ethyl acetate extract is washed successively with 0.4 M potassium bisulfate, water, and 1.0 M potassium bicarbonate then dried over magnesium sufate. The solvent is removed under reduced pressure and the residue is purified by low pressure chromatography on Woelm silica gel eluting with a gradient of 100% chloroform to 5% methanol-95% chloroform to give methyl Boc-L-tyrosyl-D-methionyl-glycyl-N-methyl-L-phenylalanyl-3-amino-1-adamantanecarboxylate. 0.5 Grams of this N-protected peptide is dissolved in 5.0 ml of dioxane. To the solution is added 5.0 ml of a 6 M solution of hydrogen chloride in dioxane, and the reaction mixture is allowed to stand for one hour at room temperature. The solvent is removed under reduced pressure. The residue is shaken with diethyl ether to give a powder. Removal of the diethyl ether by filtration gives the product, methyl L-tyrosyl-D-methionyl-glycyl-N-methyl-L-phenylalanyl-3-amino-1-adamantanecarboxylate hydrochloride which is represented by the following formula

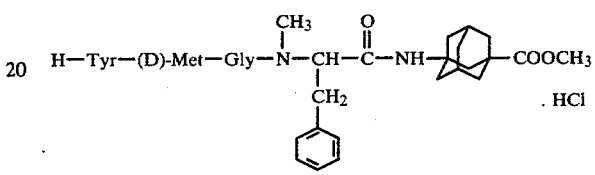

When 1.73 g of Boc-N-methyl-L-tyrosine hydroxysuccinimide ester is substituted for the Boc-L-tyrosine-pentachlorophenyl ester above and the procedure detailed substantially repeated there is obtained methyl Boc-N-methyl-L-tyrosyl-D-methionyl-glycyl-N-methyl-L-phenylalanyl-3-amino-1-adamantanecarboxylate hydrochloride. This product is purified by low pressure chromatography on Woelm silica gel eluting with a gradient of 60% chloroform-40% hexane to 100% chloroform followed by a second gradient of 100% chloroform to 5% methanol-95% chloroform. 0.55 Gram of the product is deblocked as described above to give methyl N-methyl-L-tyrosyl-D-methionyl-glycyl-N-methyl-L-phenylalanyl-3-amino-1-adamantanecarboxylate hydrochloride which is represented by the following formula

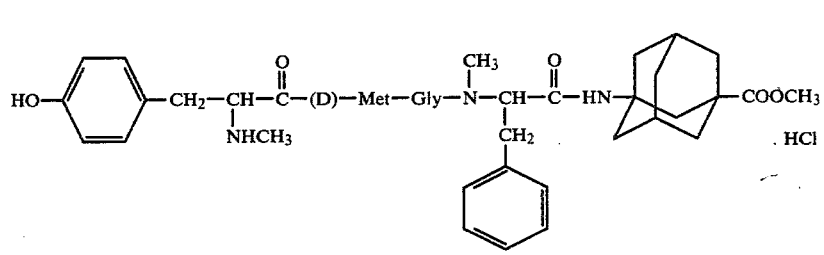

EXAMPLE 54

116 Grams of L-phenylalanine is dissolved in 1000 ml of 90% acetic acid and hydrogenated over 23 g of 5% rhodium on carbon at 40 psi and 37° C. for 24 hours. The catalyst is removed by filtration, the filtrate is concentrated to dryness under high vacuum, and the residue is crystallized from 2 liters of 15% acetic acid to give L-β-cyclohexylalanine which is represented by the following formula

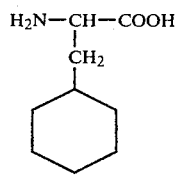

Substitution of an equivalent quantity of L-β-cyclohexylalanine for the L-phenylalanine of Example 1 and substantial repetition of the procedures detailed in Examples 1 through 9 provides methyl L-tyrosyl-D-methionyl-glycyl-L-β-cyclohexylalanyl-3-amino-1-adamantanecarboxylate hydrochloride which is represented by the following formula

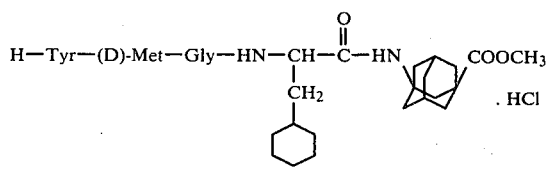

EXAMPLE 55

2-Amino-2-adamantanecarboxylic acid is prepared by the method described in H. T. Nogasawa, et. al., J. MED. CHEM., 16: 823 (1973). When an equivalent quantity of 2-amino-2-adamantanecarboxylic acid is substituted for the 3-amino-1-adamantanecarboxylic acid of Example 1 and the procedures detailed in Examples 1 through 9 substantially repeated there is obtained methyl L-tyrosyl-D-methionyl-glycyl-L-phenylalanyl-2-amino-2-adamantanecarboxylate hydrochloride which is represented by the following formula

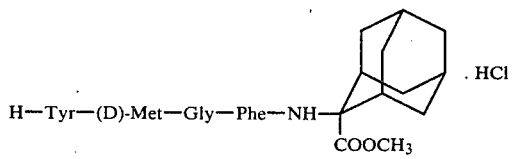

EXAMPLE 56

4.7 Grams of 4-oxo-2-adamantanecarboxylic acid [preparation is described in G. Snatzke, et. al., CHEM. BER. 100:1710–1724(1967)] is hydrogenated in 75 ml of ethanol over 0.47 g of platinum oxide in the presence of ammonia gas under 60 psi of pressure at room temperature. The solvent is removed under reduced pressure and 15 ml of water is added and removed under reduced pressure. Another 15 ml of water is added and removed under reduced pressure then the residue is dried at 100° C. in a vacuum oven for 1 hour to give 4-amino-2-adamantanecarboxylic acid which is represented by the following formula

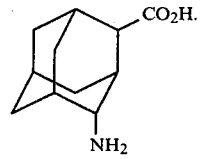

Substitution of an equivalent quantity of 4-amino-2-adamantanecarboxylic acid for the 3-amino-1-adamantanecarboxylic acid of Example 1 and substantial repetition of the procedures detailed in Examples 1 through 9 provides methyl L-tyrosyl-D-methionyl-glycyl-L-phenylalanyl-4-amino-2-adamantanecarboxylate hydrochloride which is represented by the following formula

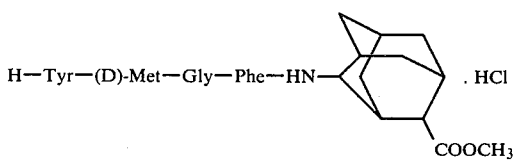

EXAMPLE 57

19.4 Grams of 2-oxo-1-adamantanecarboxylic acid is refluxed with 25 ml of thionyl chloride for one hour. The thionyl chloride is removed under reduced pressure and toluene is added and removed under reduced pressure to remove any excess thionyl chloride. The residue is dissolved in diethyl ether and ammonia gas is passed over the solution until the exothermic reaction stops. The solid is collected by filtration and washed with diethyl ether to give 2-oxoadamantane-1-carboxamide which is represented by the following formula

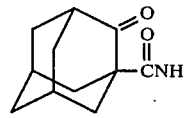

To a solution of 19.3 g of 2-oxoadamantane-1-carboxamide and 10.9 g sodium methoxide in 100 ml of methanol at 10° C. is added dropwise a solution of 23.97 g of bromine in 25 ml of methanol while maintaining the temperature at 10° C. The reaction mixture is warmed to room temperature and stirred overnight then poured into water and partitioned between methylene chloride and water. The organic layer is separated, washed with water and dried over magnesium sulfate. The solvent is removed under reduced pressure to give methyl 2-oxoadamantane-1-carbamate and 22.3 g of this compound is dissolved in 100 ml of diethyl ether. This solution is added dropwise to a mixture of 86.9 g of n-butyllithium and 61.7 g of methoxymethyl-triphenyl phosphonium chloride in 1.0 liter of diethyl ether. The reaction mixture is stirred overnight, 40.88 g of zinc chloride is added, and the mixture is stirred one hour then filtered. The solvent is removed under reduced pressure, and the residue is dissolved in 90% acetic acid. After stirring for 18 hours the reaction mixture is poured into water and extracted three times with 150 ml portions of diethyl ether. The combined ether layers are washed with saturated sodium bicarbonate until they are neutral then dried over magnesium sulfate. The solvent is removed under reduced pressure and the residue is dissolved in acetone. Enough Jones reagent is added to maintain a red color for one minute then isopropyl alcohol is added to destroy any excess Jones reagent. The acetone is removed under reduced pressure and 150 ml of water is added. The solid is filtered, washed with water, dissolved in 100 ml of 5% hydrochloric acid and warmed on the steam bath for ½ hour. The pH is adjusted to 7 with sodium hydroxide and the product is collected by filtration and dried to give 1-amino-2-adamantanecarboxylic acid which is represented by the following formula

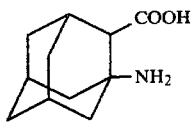

Substitution of an equivalent quantity of 1-amino-2-adamantanecarboxylic acid for the 3-amino-1-adamantanecarboxylic acid of Example 1 and substantial repetition of the procedures detailed in Examples 1 through 9 provides methyl L-tyrosyl-D-methionyl-glycyl-L-phenylalanyl-1-amino-2-adamantanecarboxylate hydrochloride which is represented by the following formula

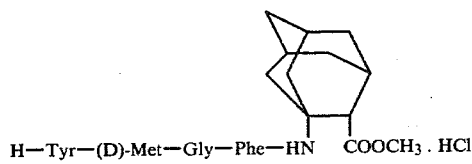

H—Tyr—(D)-Met—Gly—Phe—HN    COOCH$_3$ . HCl

EXAMPLE 58

A solution of 1.2 g of nitryltetrafluoroborate in 15 ml of acetonitrile is cooled to 0° C. and a solution of 2.17 g of 5-bromo-2-oxoadamantane [preparation is described in H. W. Geluk, SYNTHESIS, p. 374 (1972)] in 15 ml of acetonitrile is added with rapid stirring and cooling. The reaction mixture is stirred for 30 minutes then poured into water and extracted with diethyl ether. The diethyl ether extract is washed with 5% sodium bicarbonate solution and water and dried over magnesium sulfate. The solvent is removed under reduced pressure to give N-(2-oxoadamantan-5-yl)acetamide. Substitution of an equivalent quantity of N-(2-oxoadamantan-5-yl)acetamide for the methyl 2-oxoadamantane-1-carbamate of Example 57 and substantial repetition of the procedures detailed therein provides methyl L-tyrosyl-D-methionylglycyl-L-phenylalanyl-5-amino-2-adamantanecarboxylate hydrochloride which is represented by the formula

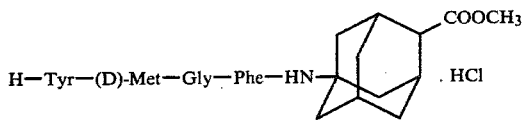

H—Tyr—(D)-Met—Gly—Phe—HN    COOCH$_3$  . HCl

EXAMPLE 59

To a solution of 5.98 g of 3-amino-1-adamantanecarboxylic acid in 40 ml of dry tetrahydrofuran stirred under a nitrogen atmosphere is added 6.5 ml of boron trifluoride etherate. Stirring is continued as 35 ml of a 1 M solution of borane in tetrahydrofuran is added at a rate which maintains reflux. The reaction mixture is refluxed for 4.5 hours then cooled and 20 ml of a 4 N solution of sodium hydroxide is added dropwise. The upper phase, which contains the tetrahydrofuran and the borate ester of the product, is separated. The tetrahydrofuran is removed under reduced pressure, and the residue is heated with 40 ml of a 4 N sodium hydroxide solution for 24 hours at 100° C. The solution is extracted three times with 200 ml of chloroform. The combined chloroform extracts are dried over potassium carbonate and the solvent is removed under reduced pressure. The residue is stirred with diethyl ether to give a crystalline product, 3-amino-1-adamantanemethanol which is represented by the following structure

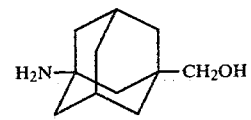

To a solution of 1.83 g of Boc-L-phenylalanine in 15 ml of dimethylformamide is added 0.76 of N-methylmorpholine. The reaction mixture is cooled to −40° C. and 0.90 ml of isobutylchloroformate is added with stirring. The reaction mixture is stirred for 15 minutes at a temperature below −10° C. then 1.04 g of 3-amino-1-adamantanemethanol is added. The reaction mixture is stirred for 15 minutes at −20° C. then stored overnight at 5° C. The dimethylformamide is removed under reduced pressure and the residue is dissolved in methylene chloride and water. The methylene chloride phase is separated and washed twice with 35 ml of water, 3 times with 35 ml of a 0.5 M potassium bisulfate solution, and twice with 35 ml of water and then dried over magnesium sulfate. The solvent is removed under reduced pressure, and the residue is purified by chromatography on Whatman 10 micron silica gel eluting with a gradient of 1:1 hexane-chloroform to chloroform to give Boc-L-phenylalanyl-3-amino-adamantanemethanol. 2.0 Grams of this product is dissolved in 5 ml of a 6 N solution of hydrogen chloride in dioxane. The reaction mixture is allowed to stand for 20 minutes at room temperature then the solvent is removed under reduced pressure at 30° C., and the residue is stirred with diethyl ether to give the product as a solid. The solid product is collected by filtration and dried under reduced pressure to give L-phenylalanyl-3-amino-1-adamantanemethanol hydrochloride which is represented by the following structure

When an equivalent quantity of L-phenylalanyl-3-amino-1-adamantanemethanol hydrochloride is substituted for the methyl L-phenylalanyl-3-amino-1-adamantanecarboxylate hydrochloride of Example 4 and the procedures detailed in Examples 4 through 9 substantially repeated there is obtained L-tyrosyl-D-methionyl-glycyl-L-phenylalanyl-3-amino-1-adamantanemethanol hydrochloride which is represented by the following formula

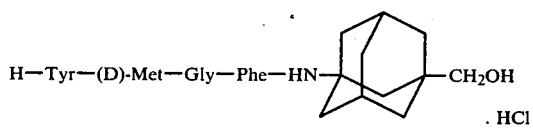

EXAMPLE 60

When an equivalent quantity of Boc-D-proline or Boc-L-proline is substituted for the Boc-D-alanine of Example 41 and the procedures detailed in Examples 41 through 48 are substantially repeated there is obtained methyl L-tyrosyl-D-prolyl-glycyl-L-phenylalanyl-3-amino-1-adamantanecarboxylate hydrochloride or methyl L-tyrosyl-L-prolyl-glycyl-L-phenylalanyl-3-amino-1-adamantanecarboxylate which are represented by the formulas

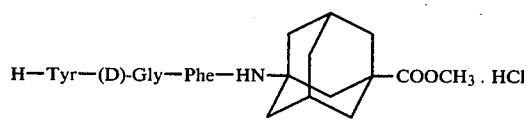

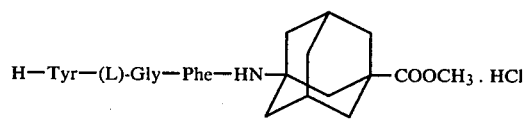

EXAMPLE 61

Substitution of an equivalent quantity of 1-(aminomethyl)adamantane for the 1-aminoadamantane of Example 24 and substantial repetition of the procedures detailed in Examples 24 and 25 provides L-phenylalanyl-1-(aminomethyl)adamantane. Substitution of an equivalent quantity of L-phenylalanyl-1-(aminomethyl)adamantane for the L-phenylalanyl-L-aminoadamantane of Example 31 and substantial repetition of the procedures detailed in Examples 31 and 32 provides L-tyrosyl-D-methionyl-glycyl-L-phenylalanyl-1-(aminomethyl)adamantane hydrochloride which is represented by the following formula

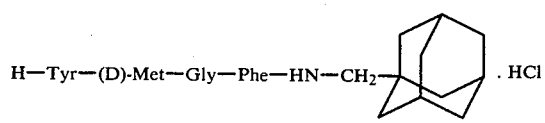

What is claimed is:
1. A compound of the formula

wherein W represents tyrosine or a radical of the formula

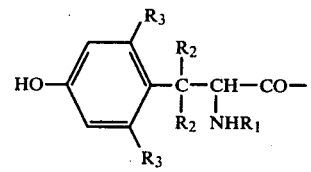

wherein
- $R_1$, $R_2$, and $R_3$ may each independently be hydrogen or an alkyl group having 1 to 4 atoms;
- X represents methionine, methionine sulfoxide, dehydro-α-aminobutyric acid, 1-aminocyclopropane carboxylic acid, alanine, O-methylhomoserine, proline or norleucine;
- Y represents phenylalanine, dehydrophenylalanine, cyclohexylalanine, or a radical of the formula

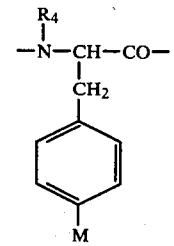

wherein $R_4$ represents hydrogen or an alkyl group having 1 to 4 carbon atoms, and M represents hydrogen, nitro or halogen;
Z represents a radical of the formula

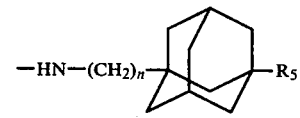

wherein $R_5$ represents hydrogen, carboxyl, methoxycarbonyl, carboxamide, or hydroxymethyl, and n is 0, 1, or 2; a radical of the formula

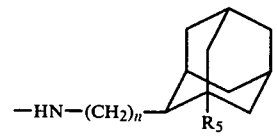

wherein $R_5$ and n are defined as hereinbefore; a radical of the formula

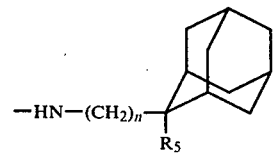

wherein $R_5$ and n are defined as hereinbefore; a radical of the formula

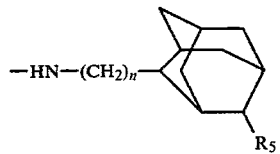

wherein $R_5$ and n are defined as hereinbefore; a radical of the formula

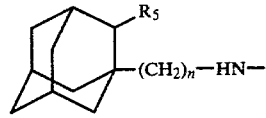

wherein $R_5$ and n are defined as hereinbefore; or a radical of the formula

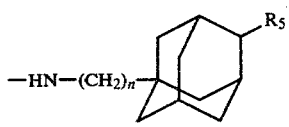

wherein $R_5$ and n are defined as hereinbefore; the stereochemical configuration of each of the optically active amino acid residues may independently be D, L or DL; and the pharmacologically acceptable salts thereof.

2. A compound according to claim 1 of the formula

W—X—Gly—Y—Z wherein W represents tyrosine or a radical of the formula

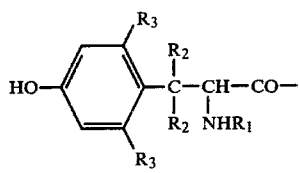

wherein $R_1$, $R_2$, and $R_3$ may each independently be hydrogen or an alkyl group having 1 to 4 carbon atoms;

X represents methionine, methionine sulfoxide, dehydro-α-amino-butyric acid, 1-aminocyclopropane carboxylic acid, alanine, O-methylhomoserine, proline or norleucine;

Y represents phenylalanine, dehydrophenylalanine, cyclohexylalanine or a radical of the formula

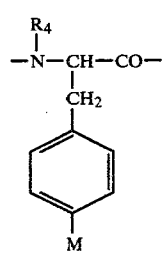

wherein $R_4$ represents hydrogen or an alkyl group having 1 to 4 carbon atoms, and M represents hydrogen, nitro, or halogen;

Z represents a radical of the formula

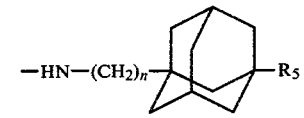

wherein $R_5$ represents hydrogen, carboxyl, methoxycarbonyl, carboxamide or hydroxmethyl, and n is 0, 1 or 2; the stereochemical configuration of each of the optically active amino acid residues may independently be D, L or DL; and the pharmacologically acceptable salts thereof.

3. A compound according to claim 2 of the formula

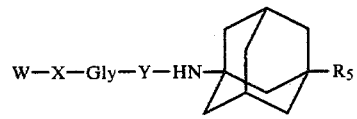

wherein W represents tyrosine or a radical of the formula

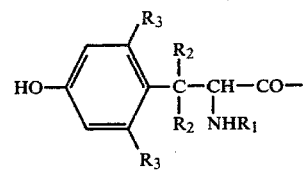

wherein $R_1$, $R_2$, and $R_3$ may each independently be hydrogen, or an alkyl group having 1 to 4 carbon atoms;

X represents methionine, methionine sulfoxide, dehydro-α-aminobutyric acid, 1-aminocyclopropane carboxylic acid, alanine, O-methylhomoserine, proline or norleucine;

Y represents phenylalanine, dehydrophenylalanine, cyclohexylalanine, or a radical of the formula

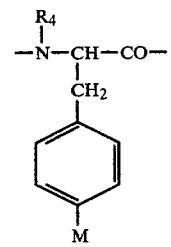

wherein $R_4$ represents hydrogen or an alkyl group having 1 to 4 carbon atoms, and M represents hydrogen, nitro or halogen; $R_5$ represents hydrogen or methoxycarbonyl; and the stereochemical configuration of each of the optically active amino acid residues may independently be D, L or DL; and the pharmacologically acceptable salts thereof.

4. A compound according to claim 2 of the formula

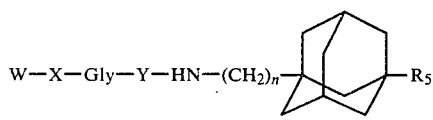

wherein W represents tyrosine, 2,6-dimethyltyrosine, β,β-dimethyltyrosine or N-methyltyrosine;
X represents methionine, methionine sulfoxide, 1-aminocyclopropane carboxylic acid, alanine, proline, or norleucine;
Y represents phenylalanine, N-methylphenylalanine or p-nitrophenylalanine;
$R_5$ represents hydrogen, carboxyl, methoxycarbonyl, carboxamide, or hydroxymethyl and n is 0 or 1; the stereochemical configuration of each of the optically active amino acid residues may independently be D, L or DL; and the pharmacologically acceptable salts thereof.

5. A compound according to claim 2 of the formula

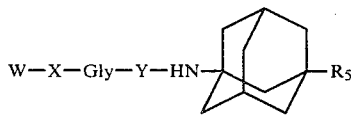

wherein W represents tyrosine, 2,6-dimethyltyrosine, β,β-dimethyltyrosine or N-methyltyrosine;
X represents methionine, methionine sulfoxide, 1-aminocyclopropane carboxylic acid, alanine, proline or norleucine;
Y represents phenylalanine, N-methylphenylalanine or p-nitrophenylalanine;
$R_5$ represents hydrogen or methoxycarbonyl; the stereochemical configuration of each of the optically active amino acid residues may independently be D, L or DL; and the pharmacologically acceptable salts thereof.

6. A compound according to claim 4 of the formula

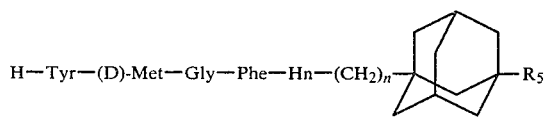

wherein $R_5$ represents hydrogen, carboxyl, methoxycarbonyl, carboxamide, or hydroxymethyl and n is 0 or 1; the stereochemical configuration of each of the optically active amino acid residues may independently be D, L or DL; and the pharmacologically acceptable salts thereof.

7. A compound according to claim 1 of the formula

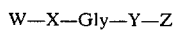

wherein W represents tyrosine or a radical of the formula

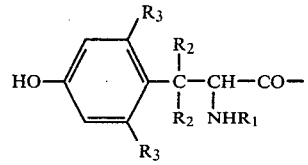

wherein $R_1$, $R_2$, and $R_3$ may each independently be hydrogen or an alkyl group having 1 to 4 carbon atoms;
X represents methionine, methionine sulfoxide, dehydro-α-aminobutyric acid, 1-aminocyclopropane carboxylic acid, alanine, O-methylhomoserine, proline or norleucine;
Y represents phenylalanine, dehydrophenylalanine, cyclohexylalanine or a radical of the formula

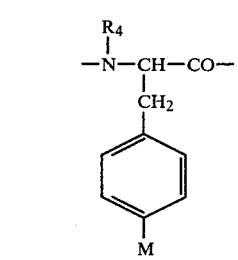

wherein $R_4$ represents hydrogen or an alkyl group having 1 to 4 carbon atoms, and M represents hydrogen, nitro or halogen;
Z represents a radical of the formula

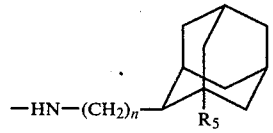

wherein $R_5$ represents hydrogen, carboxyl, methoxycarbonyl, carboxamide or hydroxymethyl, and n is 0, 1 or 2; the stereochemical configuration of each of the optically active amino acid residues may independently be D, L, or DL; and the pharmacologically acceptable salts thereof.

8. A compound according to claim 7 of the formula

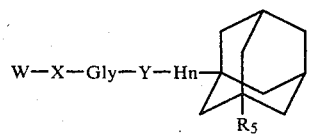

wherein W represents tyrosine or a radical of the formula

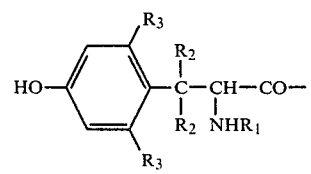

wherein $R_1$, $R_2$, and $R_3$ may each independently be hydrogen or an alkyl group having 1 to 4 carbon atoms;

X represents methionine, methionine sulfoxide, dehydro-α-aminobutyric acid, 1-aminocyclopropane carboxylic acid, alanine, O-methylhomoserine, proline or norleucine;

Y represents phenylalanine, dehydrophenylalanine, cyclohexylalanine, or a radical of the formula

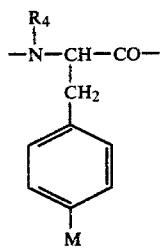

wherein $R_4$ represents hydrogen or an alkyl group having 1 to 4 carbon atoms, and M represents hydrogen, nitro, or halogen; $R_5$ represents hydrogen or methoxycarbonyl; and the stereochemical configuration of each of the optically tive amino acid residues may independently be D, L or DL; and the pharmacologically acceptable salts thereof.

9. A compound according to claim 7 of the formula

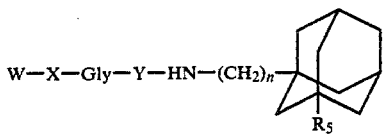

wherein W represents tyrosine, 2,6-dimethyltyrosine, β,β-dimethyltyrosine or N-methyltyrosine;

X represents methionine, methionine sulfoxide, 1-aminocyclopropane carboxylic acid, alanine, proline, or norleucine;

Y represents phenylalanine, N-methylphenylalanine, or p-nitrophenylalanine;

$R_5$ represents hydrogen, carboxyl, methoxycarbonyl, carboxamide or hydroxymethyl and n is 0 or 1; the stereochemical configuration of each of the optically active amino acid residues may independently be D, L or DL; and the pharmacologically acceptable salts thereof.

10. A compound according to claim 7 of the formula

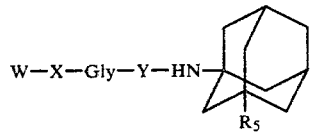

wherein W represents tyrosine, 2,6-dimethyltyrosine, β,β-dimethyltyrosine, or N-methyltyrosine;

X represents methionine, methionine sulfoxide, 1-aminocyclopropane carboxylic acid, alanine, proline or norleucine;

Y represents phenylalanine, N-methylphenylalanine, or p-nitrophenylalanine;

$R_5$ represents hydrogen or methoxycarbonyl; the stereochemical configuration of each of the optically active amino acid residues may independently be D, L or DL; and the pharmacologically acceptable salts thereof.

11. A compound according to claim 7 of the formula

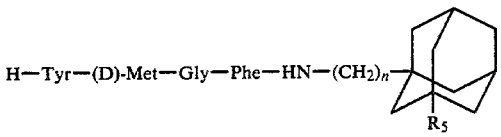

wherein R represents hydrogen, carboxyl, methoxycarbonyl, carboxamide or hydroxymethyl, and n is 0 or 1; and the stereochemical configuration of each of the optically active amino acid residues may independently be D, L or DL; and the pharmacologically acceptable salts thereof.

12. A compound according to claim 1 which is methyl L-tyrosyl-D-methionyl-glycyl-L-phenylalanyl-3-amino-1-adamantanecarboxylate sulfoxide.

13. A compound according to claim 1 which is L-tyrosyl-D-methionyl-glycyl-L-phenylalanyl-1-aminoadamantane.

14. A compound according to claim 1 which is methyl 2,6-dimethyl-DL-tyrosyl-D-methionyl-glycyl-L-phenylalanyl-3-amino-1-adamantanecarboxylate.

15. A compound according to claim 1 which is methyl L-tyrosyl-D-norleucyl-glycyl-L-phenylalanyl-3-amino-1-adamantanecarboxylate.

16. A compound according to claim 1 which is methyl L-tyrosyl-D-methionyl-glycyl-N-methyl-L-phenyl-alanyl-3-amino-1-adamantanecarboxylate.

17. A compound according to claim 1 which is methyl N-methyl-L-tyrosyl-D-methionyl-glycyl-N-methyl-L-phenylalanyl-3-amino-1-adamantanecarboxylate.

* * * * *